(12) United States Patent
Schweinsberg et al.

(10) Patent No.: US 8,790,628 B2
(45) Date of Patent: *Jul. 29, 2014

(54) COMPOSITION FOR SHAPING KERATIN FIBERS CONTAINING STARCHES MODIFIED WITH PROPYLENE OXIDE

(75) Inventors: Matthias Schweinsberg, Hamburg (DE); Thorsten Knappe, Schenefeld (DE); Ralf Roenisch, Wuppertal (DE); Mathias Schriefers, Moenchengladbach (DE); Carine Dogan, Vigneux sur Seine (FR)

(73) Assignee: Henkel AG & Co. KGaA, Dusseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/452,174

(22) Filed: Apr. 20, 2012

(65) Prior Publication Data

US 2012/0201774 A1     Aug. 9, 2012

Related U.S. Application Data

(63) Continuation of application No. PCT/EP2010/065863, filed on Oct. 21, 2010.

(30) Foreign Application Priority Data

Oct. 22, 2009  (DE) .......................... 10 2009 045 933

(51) Int. Cl.
*A61K 8/73* (2006.01)
*A61K 8/86* (2006.01)
*A61K 8/00* (2006.01)

(52) U.S. Cl.
USPC ..................... 424/70.13; 424/70.11; 424/70.1

(58) Field of Classification Search
USPC ................................. 424/70.13, 70.11, 70.1
See application file for complete search history.

(56) References Cited

U.S. PATENT DOCUMENTS

| | | | |
|---|---|---|---|
| 4,528,283 A | 7/1985 | Lang et al. | |
| 4,780,310 A | 10/1988 | Lang et al. | |
| 4,976,952 A | 12/1990 | Lang et al. | |
| 5,520,200 A | 5/1996 | Sturla | |
| 6,235,913 B1 | 5/2001 | Raths et al. | |
| 6,344,183 B2 * | 2/2002 | Paul et al. | 424/47 |
| 6,365,140 B1 | 4/2002 | Melby et al. | |
| 6,413,505 B1 | 7/2002 | Vitale et al. | |
| 7,205,271 B2 * | 4/2007 | Drzewinski et al. | 510/475 |
| 7,332,466 B2 | 2/2008 | Schmid et al. | |
| 2006/0013785 A1 | 1/2006 | Lauscher et al. | |

FOREIGN PATENT DOCUMENTS

| | | |
|---|---|---|
| AU | 730455 B2 | 5/2000 |
| DE | 19756454 C1 | 6/1999 |
| DE | 10352470 A1 | 6/2005 |
| EP | 0274086 A2 | 7/1988 |
| EP | 0580514 A1 | 1/1994 |
| EP | 0838212 A1 | 4/1998 |
| EP | 0948958 A2 | 10/1999 |
| EP | 0948959 A2 | 10/1999 |
| EP | 0948960 A2 | 10/1999 |
| EP | 1317916 A2 | 6/2003 |
| WO | 02083089 A1 | 10/2002 |

OTHER PUBLICATIONS

Gottschalck, T.E. et al. "International Cosmetic Ingredient Dictionary and Handbook." The Cosmetic, Toiletry and Fragrance Association, 12th Edition, vol. 3, 2008, pp. 3187-3192 and 3214-3215, XP002627782.
National Starch and Chemical, "Personal Care Polymers" (2000).
Reiger, "Hair Setting Products", Harry's Cosmeticology, vols. I-II (8th Edition), Chapter 30, Chemical Publishing Company Inc., pp. 635-667 (2000).

* cited by examiner

*Primary Examiner* — Gina C Justice
(74) *Attorney, Agent, or Firm* — Ingrassia Fisher & Lorenz, P.C.

(57) ABSTRACT

Cosmetic products for temporary deformation of keratinic fibers, containing, in a cosmetic carrier present in the form of a dispersed system, at least one starch modified with propylene oxide and having an average molecular weight (weight average) of from 50 to 2500 kDa, the products providing a hairstyle with a strong hold and high flexibility. The starches modified with propylene oxide are based on renewable raw materials. In this way, effective styling agents for hair can be provided and the content of polymeric raw materials based on fossil fuels reduced.

17 Claims, No Drawings

COMPOSITION FOR SHAPING KERATIN FIBERS CONTAINING STARCHES MODIFIED WITH PROPYLENE OXIDE

CROSS REFERENCE TO RELATED APPLICATIONS

The present application is a continuation of International Application No. PCT/EP2010/065863 filed 21 Oct. 2010, which claims priority to German Patent Application No. 10 2009 045 933.2 filed 22 Oct. 2009, both of which are incorporated herein by reference.

The present invention relates to cosmetic agents for temporary deformation of keratinic fibers containing, in a cosmetic carrier present in the form of a dispersed system, at least one starch modified with propylene oxide and having an average molecular weight (weight average) from 50 to 2500 kDa.

Styling agents for deformation of keratinic fibers have been known from some time and are used in various embodiments to build up, refresh, and fix in place hairstyles that, for many types of hair, can be obtained only with use of setting active substances. An important role is played in this context both by hair treatment agents that serve for permanent shaping, and those serving for temporary shaping of the hair. Temporary shaping operations that are intended to yield good hold without impairing the healthy appearance of the hair such as its shine, can be achieved, for example, using hair sprays, hair waxes, hair gels, blow-dry waves, etc.

Corresponding agents for temporary shaping usually contain synthetic polymers as a shaping component. Preparations having a dissolved or dispersed polymer can be applied onto hair using propellant gases or a pump mechanism. Hair gels and hair waxes, however, are not applied directly onto the hair but instead distributed in the hair using a comb or one's hands.

Synthetic polymers typically used in agents for temporary shaping are manufactured from corresponding synthetically accessible monomers. These monomers are obtained from fossil substances such as petroleum by conversion to the corresponding polymer modules, in some cases with expenditure of energy.

In a more sustainable approach to nature as living space, and to resources, it is still desirable to use for cosmetic products only those cosmetic raw materials that are accessible, with as little energy use as possible, from renewable raw materials. A reduction in the quantity, or even a replacement, of synthetic polymers can be undertaken, however, only when the substitute exhibits those properties desired for the intended application, and ensures a sufficiently stable hold and shape for the keratin-containing fibers.

In addition, nature-based substitute polymers should retain the elasticity and smoothness of keratin-containing fibers that are fixed as to shape. Formation on the keratin-containing fibers of polymer particles visible to the naked eye must be avoided. In addition, the keratin-containing fibers must not give a dull impression, but should have a natural shine.

The present invention therefore provides a cosmetic composition acting in shape-fixing fashion so that predominantly renewable raw materials are used for shape fixing. The composition further provides improved shape fixing, and does not exhibit the disadvantages recited above.

A first subject of the invention is therefore a cosmetic agent for temporary deformation of keratinic fibers, particularly human hair, containing, in a cosmetic carrier present in the form of a dispersed system, at least one starch modified with propylene oxide having an average molecular weight (weight average) from 50 to 2500 kDa. These agents have outstanding parameters for use on hair. The starch can be incorporated into the agents almost without the use of heat, at a maximum of 30° C., simply by mixing.

"Keratinic fibers" according to the present invention refer to furs, wool, feathers, and particularly human hair.

The cosmetic carrier per se (i.e., without the aforesaid starch modified with propylene oxide) is present as a dispersed system. A "dispersed system" is a system made up of multiple phases, so that in a continuous liquid phase a further phase in the form of a solid, liquid and/or gas is present in a manner finely and almost homogeneously distributed over the continuous phase. The cosmetic carrier is present in particular in cream, gel or foam form.

A "cream" according to the present invention is a composition in the form of a dispersed system having, besides water, additionally fat and/or oil. Preferably suitable fats or oils are described in the course of this application (see below).

A "gel" according to the present invention is a dimensionally stable, readily deformable, and dispersed system comprising a colloidally divided substance having long or highly branched particles and a liquid as a dispersion agent. Polymeric thickening agents preferably serve as long or highly branched particles (see below).

"Foam" according to the present invention is a dispersed system in which a gas is present as a divided phase in a liquid as a continuous phase.

Agents according to the present invention contain active substances in the form of a cosmetic carrier present in the form of a dispersed system, preferably in
 a water-containing cosmetic carrier present in the form of a dispersed system,
 an alcoholic cosmetic carrier present in the form of a dispersed system, or
 an aqueous alcoholic cosmetic carrier present in the form of a dispersed system.

The dispersed system for these carriers is, as indicated above, preferably chosen from among cream, gel, and foam.

"Aqueous alcoholic" carriers for purposes of the present invention are aqueous compositions containing 3 to 70 wt % of a $C_1$ to $C_4$ alcohol, particularly ethanol or isopropanol. The agents can additionally contain other organic solvents such as methoxybutanol, benzyl alcohol, ethyl diglycol, 1,2-propylene glycol, or 1,3-propylene glycol. All water-soluble organic solvents are preferred in this context.

The agent according to the present invention contains, in the cosmetic carrier, a specific starch derivative.

Starch is a reserve carbohydrate that is stored by many plants in the form of large starch grains (granules), usually 1 to 200 µm in size, in various parts of the plant, for example, in tubers or roots, cereal seeds, fruits and in the pith. A starch modified with propylene oxide that can be used according to the invention can be obtained from the starch of potatoes, corn, rice, peas, acorns, chestnuts, barley, wheat, bananas, sago, millet, sorghum, oats, barley, rye, beans, yams, arrowroot or cassava. Particularly pronounced effects according to the present invention are achieved with tapioca starch modified with propylene oxide or a potato starch modified with propylene oxide or with mixtures of the two aforesaid starches. Very preferably, the agent according to the invention contains at least one potato starch modified with propylene oxide.

Starch belongs to the homoglycan family and is a polycondensation product of D-glucose. Starch is made up of three structurally different polymers of d-glucopyranose, namely amylose, amylopectin, and an intermediate fraction. Higher plants contain 0 to 45 wt % amylose, based on the dry substance.

The intermediate fraction, also referred to as "anomalous amylopectin," is structurally intermediate between amylose and amylopectin. The quantitative indications defined in the context of this application for amylopectin include the intermediate fraction.

It is preferred if the starch modified with propylene oxide has an amylose content of less than 25 wt %, particularly less than 20 wt %, based on weight of the starch. Starch containing 17 to 22 wt % amylose and 78 to 83 wt % amylopectin is particularly suitable for achieving the effect according to the present invention.

Amylose is made up of predominantly linear α-1,4-glycosidically linked d-glucose, $M_r$ 50,000 to 150,000. The resulting chains form double helices in the starch.

Amylopectin also contains, in addition to the α-1,4 links described for amylose, α-1,6 bonds (in an amount from 4 to 6%) as branching points. The average spacing between the branching points is approximately 12 to 17 glucose units. The molar mass of $10^7$ to $7*10^8$ corresponds to approximately $10^5$ glucose units, making amylopectin one of the largest biopolymers. The branching points are distributed over the molecule in such a way that a bundle structure with relatively short side chains develops. Each double helix is formed by two of these side chains. As a result of the many branching points, amylopectin is relatively easily soluble in water.

"Starch modified with propylene oxide" according to the present invention is a reaction product of a starch with propylene oxide. A reaction product of this kind includes at least one structural unit of formula (PS)

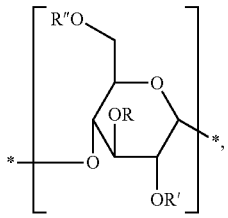

(PS)

wherein at least one of R, R', or R" is a group of the formula

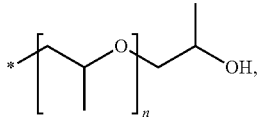

wherein n is greater than or equal to zero, and at most two of R, R', and R" is a hydrogen atom. Starches modified with propylene oxide are provided, for example, by reacting a natural starch with propylene oxide. Before modification with propylene oxide, the starch can have been exposed to a variety of physical or chemical processes, for example, heat treatment, shear, thermal, acid-hydrolytic, oxidizing, or enzymatic cleavage, etc.

It is preferred if the starch modified with propylene oxide is not present in the agent according to the present invention in the form of individual starch grains (granules). For this purpose, the starch grains are disintegrated, for example, by heat or shear, and the corresponding polysaccharide molecules are released from the composite material. The released polysaccharide molecules are modified with propylene oxide after or before release.

Starches according to the present invention modified with propylene oxide are present in the agent in a molecular weight distribution. The molecular weight distribution is determined experimentally by gel filtration chromatography against dextran. An important feature of the invention is the weight average of the average molecular weight of the propylene oxide-modified starches contained in the agent according to the present invention. The weight average is an average molecular weight that takes into account total weight of the molecules of various molecular weights, and not simply the number of molecules.

For statistical calculation of the weight average, firstly the "weight break" is defined:

$$w_i = (N_i M_i)/[\Sigma(N_i M_i)].$$

This indicates the weight proportion, in the sample, of macromolecules made up of i segments (e.g., monomer modules) of mass $M_i$ and that occur $N_i$ times in the sample. The weight average of molecular weight $M_w = \Sigma w_i M_i$ is thus given by $$M_w = [\Sigma(N_i M^2_i)]/[\Sigma(N_i M_i)].$$

Preferred agents according to the present invention preferably contain starches modified with propylene oxide having an average molecular weight (weight average) from 100 to 2000 kDa, particularly from 500 to 1800 kDa, very preferably from 700 to 1000 kDa. The agents of this embodiment are incorporated preferably into foams or gels as a cosmetic carrier, and are therefore present as a foam or gel.

Average molecular weights (weight average) from 100 to 400 kDa, particularly from 200 to 300 kDa, are likewise preferably suitable for agents according to the present invention. Agents of this embodiment are incorporated preferably into foams or gels as a cosmetic carrier, and are therefore present as a foam or gel. Despite a molecular weight that is low for setting polymers, outstanding setting can be achieved with these starches. In addition, gels manufactured with the starches achieve superb transparency.

In order to adjust the molecular weight, the starch is subjected to mechanical and/or chemical treatment before or after modification with propylene oxide. To elevate the molecular weight, the starch can be crosslinked. Crosslinking of the starch modified with propylene oxide exists when the linear or branched polysaccharide macromolecules of the starch are linked covalently by a crosslinking agent, forming a three-dimensional, insoluble, and still swellable polymeric network. Natural starch is generally considered uncrosslinked and, if crosslinking is desirable, requires artificial crosslinking by synthesis chemistry. Artificial crosslinking of this kind can be carried out using crosslinking agents. Starches (modified with propylene oxide) that do not exhibit such crosslinking are uncrosslinked.

Crosslinking occurs, for example, using the crosslinking agent epichlorohydrin. For this, a 42-wt % mixture of starch modified with propylene oxide in water is produced, into which the desired amount of epichlorohydrin is stirred at room temperature. Once target viscosity is reached after a stirring time of 1 to 5 hours with viscosity monitoring, the crosslinked starch is isolated using ordinary methods.

It is preferred, however, if the agents contain an uncrosslinked starch modified with propylene oxide.

To achieve a lower molecular weight, particularly from 100 to 400 kDa or 200 to 300 kDa, the starches are preferably exposed to mechanical cleavage, enzymatic cleavage (particularly using alpha-amylase, beta-amylase, glucoamylase, or debranching enzymes), acid-hydrolytic cleavage (particularly using hydrochloric acid, sulfuric acid, or phosphoric acid), thermal cleavage, or a reaction with oxidizing agents (such as periodate, hypochlorite, chromic acid, permanganate, nitrogen dioxide, hydrogen peroxide, or organic percarboxylic acid, preferably with hydrogen peroxide). Kneaders, extruders, stator/rotor mechanisms, and/or agitators are suitable for mechanical cleavage of the starch.

Oxidative cleavage using hydrogen peroxide is preferred. Here, for example, the starch modified with propylene oxide is added to water, heated to 50 to 70° C., hydrogen peroxide is added, and stirring occurs at 70 to 85° C. for 2 to 5 hours.

Propylene oxide content of the starch affects the fine-tuning of the hairstyle hold and hairstyle flexibility, as well as stability of the cosmetic agents. The parameters can be further optimized if the starch modified with propylene oxide has, based on weight of the starch, a propylene oxide content preferably from 1 to 20 wt %, particularly from 5 to 15 wt %, more preferably a propylene oxide content from 4 to 12 wt %, very particularly preferably a propylene oxide content from 9.5 to 10.5 wt % or 4 to 6 wt %. Propylene oxide content can be determined, for example, by carrying out a Hodges cleavage using the method according to DIN EN 13268.

In a preferred embodiment, the starch modified with propylene oxide is gelatinized. When an aqueous suspension of starch is heated or compressed, a tangential swelling of the bodies is then observed at a critical temperature or pressure, with loss of birefringence, a change in X-ray structure, and an abrupt rise in the viscosity of the solution. This phenomenon is called "gelatinization".

Those cosmetic agents wherein the starch modified with propylene oxide has, in a 43-wt % aqueous solution, a preferred viscosity of from 150 to 1,500,000 mPa·s (Brookfield viscosimeter, spindle 7 at 20° C. and 20 rpm) are outstandingly suitable for purposes of the invention. Particularly suitable starches modified with propylene oxide have viscosities from 10,000 to 200,000 mPa·s, particularly preferably from 25,000 to 180,000 mPa·s (measured in each case under the conditions recited above).

Starch modified with propylene oxide that is particularly preferred according to the present invention is uncrosslinked, has an average molecular weight (weight average) from 100 to 2000 kDa, particularly from 500 to 1800 kDa, very particularly preferably from 700 to 1000 kDa, and has a propylene oxide content, based on weight of the modified starch, from 1 to 20 wt %, particularly from 5 to 15 wt %, particularly preferably 4 to 12 wt %, very particularly preferably 9.5 to 10.5 wt % or from 4.0 to 6.0 wt %. This is once again preferably a tapioca starch or potato starch, particularly potato starch.

Starch modified with propylene oxide that is particularly preferred according to the present invention is uncrosslinked, has an average molecular weight (weight average) from 100 to 2000 kDa, in particular from 500 to 1800 kDa, very particularly preferably from 700 to 1000 kDa, and has a propylene oxide content, based on the weight of the modified starch, from 1 to 20 wt %, particularly preferably a propylene oxide content from 4 to 12 wt %, very particularly preferably a propylene oxide content from 9.5 to 10.5 wt % or from 4.0 to 6.0 wt %. This is once again preferably a tapioca starch or potato starch, in particular a potato starch.

Potato starch modified with propylene oxide that is very particularly preferred according to the present invention is uncrosslinked, has an average molecular weight (weight average) from 100 to 2000 kDa, particularly 500 to 1800 kDa, very preferably from 700 to 1000 kDa, and has a propylene oxide content, based on weight of the modified potato starch, from 4 to 12 wt %, very preferably a propylene oxide content from 9.5 to 10.5 wt % or from 4.0 to 6.0 wt %.

It is preferred if the cosmetic agent contains starch modified with propylene oxide in an amount from 0.1 wt % to 80 wt %, particularly 0.5 wt % to 40 wt %, very particularly preferably from 2 wt % to 10 wt %, based on weight of the agent. These weight indications are particularly preferred when the agent is present in the form of a gel or a cream.

When the agent according to the present invention is present in the form of a foam, particularly in the form of an aerosol foam (see below), it contains starch modified with propylene oxide preferably in an amount from 0.1 wt % to 20 wt %, particularly 1.0 wt % to 10 wt %, more preferably from 2 wt % to 8 wt %, very particularly preferably from 3 wt % to 6 wt %, based on weight of the agent.

The cosmetic agent, when present in the form of a gel or a cream, can additionally contain at least one film-forming and/or setting polymer. A preferred provision is that the amount by weight of the additional film-forming and/or setting polymer is less than the amount by weight of starch modified with propylene oxide present. The agent contains starch modified with propylene oxide and the additional film-forming and/or setting polymers preferably in a weight ratio range from 1:1.5 to 1:10, particularly 1:2 to 1:8.

The cosmetic agent according to the present invention, if present in the form of a foam, particularly in the form of an aerosol foam (see below), can additionally contain at least one film-forming and/or setting polymer. A preferred provision is that it comprises starch modified with propylene oxide and the additional film-forming and/or setting polymers preferably in a weight ratio range from 4:1 to 1:4, particularly 3:1 to 1:3.

"Polymers" according to the present invention are compounds constructed from a plurality of molecules in which one type or several types of atoms or atom groupings ("constituent units," "basic modules," or "repeating units") are repeatedly serially arranged, and have a molecular weight of at least 10,000 g/mol. The polymers are obtained by polyreaction, the latter being capable of occurring artificially (i.e., synthetically) or naturally.

"Film-forming polymers" are those polymers that, upon drying, leave behind a continuous film on the skin, hair, or nails. Film-formers of this kind can be used in a wide variety of cosmetic products such as face masks, make-up, hair setting agents, hair sprays, hair gels, hair waxes, hair therapies, shampoos, or nail polishes. Those polymers having sufficient solubility in water, alcohol or in water/alcohol mixtures are particularly preferred. It is possible in this way to produce corresponding solutions that can easily be utilized or further processed.

"Film-forming polymers" are also those polymers that, when applied in a 0.01- to 20-wt % aqueous, alcoholic, or aqueous alcoholic solution, are capable of depositing a transparent polymer film on hair. The film-forming polymers can be charged in anionic, amphoteric, nonionic, permanently cationic, or temporarily cationic fashion.

Particularly preferably suitable for this embodiment are those agents that additionally contain at least one film-forming and/or setting polymer chosen from at least one polymer of
    nonionic polymers based on ethylenically unsaturated monomers, in particular from
        homopolymers of N-vinylpyrrolidone,
        nonionic copolymers of N-vinylpyrrolidone,
        homopolymers and nonionic copolymers of N-vinylcaprolactam,
        copolymers of (meth)acrylamide,
        polyvinyl alcohol, polyvinyl acetate, chitosan and derivatives of chitosan, cationic cellulose derivatives, cationic copolymers of 3-($C_1$ to $C_6$) alkyl-1-vinylimidazolinium, copolymers containing the structural unit of formula (M-1)

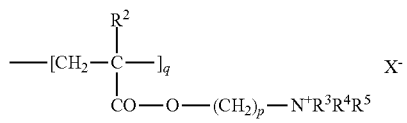
(M-1)

wherein $R^2$=—H or is —$CH_3$; $R^3$, $R^4$, and $R^5$ are, mutually independently, ($C_1$ to $C_4$) alkyl, ($C_1$ to $C_4$) alkenyl, or ($C_2$ to $C_4$) hydroxyalkyl groups; p=1, 2, 3, or 4; q is a natural number; and $X^-$ is a physiologically compatible organic or inorganic anion, anionic polymers having carboxylate groups and/or sulfonate groups, amphoteric polymers, anionic polyurethanes.

Those nonionic polymers having at least one of the following structural units

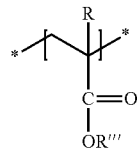
(M2)

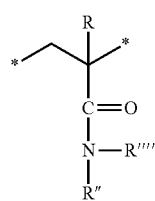
(M3)

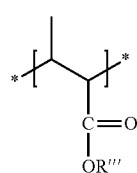
(M4)

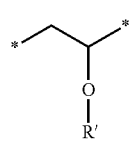
(M5)

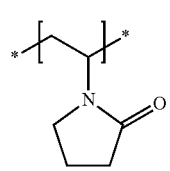
(M6)

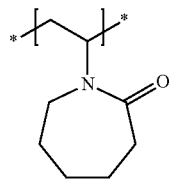
(M7)

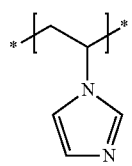
(M8)

wherein

R is a hydrogen atom or a methyl group,

R' is a hydrogen atom or a ($C_1$ to $C_4$) acyl group,

R" and R"" are, mutually independently, a ($C_1$ to $C_7$) alkyl group or a hydrogen atom, and R'" is a linear or branched ($C_1$ to $C_4$) alkyl group or a ($C_2$ to $C_4$) hydroxyalkyl group, are preferred as an additional film-forming and/or setting polymer chosen from nonionic polymers based on ethylenically unsaturated monomers.

Preferred nonionic film-forming and/or nonionic hair-setting polymers are homo- or copolymers that are constructed from at least one of the following monomers: vinylpyrrolidone, vinylcaprolactam, vinyl esters such as vinyl acetate, vinyl alcohol, acrylamide, methacrylamide, alkyl- and dialkylacrylamide, alkyl- and dialkylmethacrylamide, alkyl acrylate, alkyl methacrylate; the alkyl groups of these monomers being chosen from ($C_1$ to $C_3$) alkyl groups.

Nonionic polymers based on ethylenically unsaturated monomers and are particularly suitable for the agents according to the present invention contain at least one of the following structural units:

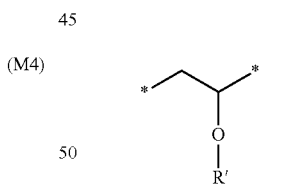
(M5)

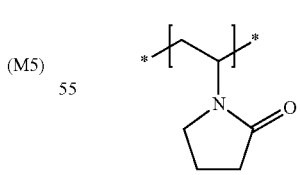
(M6)

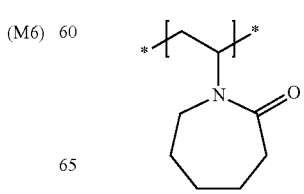
(M7)

-continued (M8)

wherein R' is a hydrogen atom or a ($C_1$ to $C_{30}$) acyl group, particularly a hydrogen atom or an acetyl group.

Homopolymers of vinyl caprolactam or vinylpyrrolidone (such as Luviskol® K 90 or Luviskol® K 85 of the BASF SE company), copolymers of vinylpyrrolidone and vinyl acetate (such as those marketed under the trademarks Luviskol® VA 37, Luviskol® VA 55, Luviskol® VA 64, and Luviskol® VA 73 by the BASF SE company), terpolymers of vinylpyrrolidone, vinyl acetate, and vinyl propionate, polyacrylamides (such as Akypomine® P 191 of the CHEM-Y company), polyvinyl alcohols (marketed, for example, under the commercial names Elvanol® of DuPont or Vinol® 523/540 of the Air Products company), terpolymers of vinylpyrrolidone, methacrylamide, and vinylimidazole (such as Luviset® Clear of the BASF SE company), are particularly suitable.

In addition to nonionic polymers based on ethylenically unsaturated monomers, nonionic cellulose derivatives are also suitable as film-forming and/or setting polymers for preferably carrying out the technical teaching and are preferably chosen from methyl cellulose, particularly from cellulose ethers such as hydroxypropyl cellulose (e.g., hydroxypropyl cellulose having a molecular weight from 30,000 to 50,000 g/mol, marketed, for example, under the commercial name Nisso SI® by the Lehmann & Voss company, Hamburg), hydroxyethyl cellulose that is marketed, for example, under the trademarks Culminal® and Benecel® (AQUALON), and Natrosol® grades (Hercules).

"Cationic polymers" are polymers having in the main chain and/or side chain a group that can be "temporarily" or "permanently" cationic. According to the present invention, those polymers having a cationic group regardless of the pH of the agent are referred to as "permanently cationic". These are polymers having a quaternary nitrogen atom, for example, in the form of an ammonium group. Preferred cationic groups are quaternary ammonium groups. Those polymers wherein the quaternary ammonium group is bonded via a C1-4 hydrocarbon group to a main polymer chain constructed from acrylic acid, methacrylic acid, or derivatives thereof have proven particularly suitable.

A preferred cationic film-forming and/or cationic setting polymer according to the present invention is at least one having at least one structural element of formula (M9) and additionally at least one structural element of formula (M10)

(M9)

-continued (M10)

wherein
R is a hydrogen atom or a methyl group,
R', R", and R''' are mutually independently a ($C_1$ to $C_{30}$) alkyl group,
X is an oxygen atom or an NH group,
A is an ethane-1,2-diyl group or a propane-1,3-diyl group,
n is 1 or 3.

All possible physiologically acceptable anions, for example, chloride, bromide, hydrogen sulfate, methyl sulfate, ethyl sulfate, tetrafluoroborate, phosphate, hydrogen phosphate, dihydrogen phosphate, or p-toluenesulfonate, triflate, serve to compensate for the positive polymer charge.

Such compounds include
  copolymers of dimethylaminoethyl methacrylate, quaternized with diethyl sulfate, with vinylpyrrolidone, having the INCI name Polyquaternium-11, under the designations Gafquat® 440, Gafquat® 734, Gafquat® 755 (each ISP company) and Luviquat PQ 11 PN (BASF SE),
  copolymers of N-vinylpyrrolidone, N-vinylcaprolactam, N-(3-dimethylaminopropyl)methacrylamide, and 3-(methacryloylamino)propyllauryldimethylammonium chloride (INCI name: Polyquaternium-69), marketed, for example, under the commercial name AquaStyle® 300 (28 to 32 wt % active substance in ethanol/water mixture) by the ISP company.

Cationic film-forming and/or cationic setting polymers are further chosen from, in particularly preferred fashion, cationic quaternized cellulose derivatives.

Cationic quaternized cellulose derivatives are further suitable as film-forming and/or setting polymers.

Those cationic quaternized celluloses having more than one permanent cationic charge in a side chain are particularly advantageous. Among these cationic celluloses, those having the INCI name Polyquaternium-4, marketed, for example, under the designations Celquat® H 100, Celquat® L 200 by the National Starch Company, are particular suitable.

Further particularly preferred cationic polymers are those cationic film-forming and/or cationic setting copolymers having at least one structural element of formula (M11)

(M11)

wherein R" is a ($C_1$ to $C_4$) alkyl group, particularly a methyl group, and
at least one additional cationic and/or nonionic structural element.

All possible physiologically acceptable anions such as chloride, bromide, hydrogen sulfate, methyl sulfate, ethyl sulfate, tetrafluoroborate, phosphate, hydrogen phosphate, dihydrogen phosphate, or p-toluenesulfonate, triflate serve to compensate for the positive polymer charge.

Preferably, at least one copolymer (c1) having in addition to at least one structural element of formula (M11) a structural element of formula (M6)

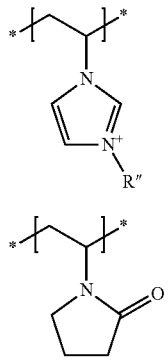

wherein R" is a ($C_1$ to $C_4$) alkyl group, particularly a methyl group, is present as an additional cationic film-forming and/or cationic setting polymer.

All possible physiologically acceptable anions such as chloride, bromide, hydrogen sulfate, methyl sulfate, ethyl sulfate, tetrafluoroborate, phosphate, hydrogen phosphate, dihydrogen phosphate, or p-toluenesulfonate, triflate, serve to compensate for the positive polymer charge of copolymers (c1).

Very particularly preferred cationic film-forming and/or cationic setting polymers as copolymers (c1) contain 10 to 30 mol %, preferably 15 to 25 mol %, and particularly 20 mol % structural units according to formula (M11), and 70 to 90 mol %, preferably 75 to 85 mol % and particularly 80 mol % structural units according to formula (M6).

It is particularly preferred if copolymers (c1) contain in addition to polymer units resulting from incorporation of the structural units according to formulae (M11) and (M6) into the copolymer, up to 5 wt %, preferably up to 1 wt %, of polymer units based on incorporation of other monomers. Copolymers (c1) are preferably constructed exclusively from structural units of formula (M11) wherein R"=methyl and (M6).

If a chloride ion is used to compensate for the positive charge of the polymer of formula (Poly-1), these N-methylvinylimidazole/vinylpyrrolidone copolymers are then referred to according to INCI nomenclature as Polyquaternium-16 and are obtainable, for example, from BASF under the trade names Luviquat® Style, Luviquat® FC 370, Luviquat® FC 550, Luviquat® FC 905, and Luviquat® HM 552.

If a methosulfate is used to compensate for the positive charge of the polymer of formula (Poly1), these N-methylvinylimidazole/vinylpyrrolidone copolymers are then referred to according to INCI nomenclature as Polyquaternium-44 and are obtainable, for example, from BASF under the trade names Luviquat® UltraCare.

Particularly preferred agents contain a copolymer (c1), particularly of formula (Poly1), having molar masses within a specific range. Agents according to the present invention in which copolymer (c1) has a molar mass from 50 to 400 kDa, preferably 100 to 300 kDa, more preferably from 150 to 250 kDa, and particularly from 190 to 210 kDa, are preferred.

In addition to or instead of copolymer or copolymers (c1), the agents can also contain copolymers (c2) that, proceeding from copolymer (c1), contain structural units of formula (M7) as additional structural units:

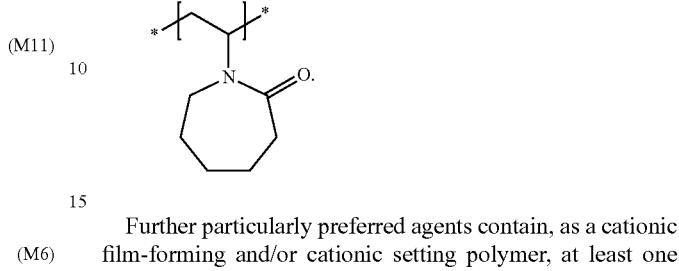

Further particularly preferred agents contain, as a cationic film-forming and/or cationic setting polymer, at least one copolymer (c2) having at least one structural unit according to formula (M11-a), at least one structural unit according to formula (M6), and at least one structural unit according to formula (M7)

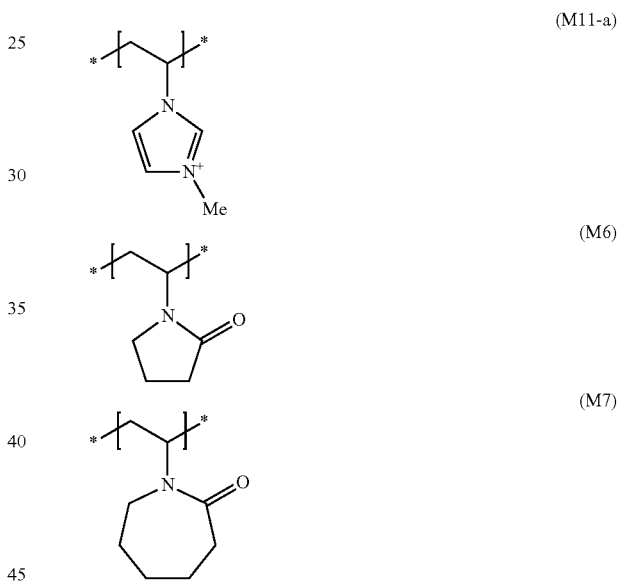

Here, it is particularly preferred if copolymers (c2) contain in addition to polymer units resulting from incorporation of the structural units according to formulae (M11-a), (M6), and (M7) into the copolymer, up to 5 wt %, preferably up to 1 wt %, of polymer units based on the incorporation of other monomers. Copolymers (c2) are preferably constructed exclusively from structural units of formulas (M11-a), (M6), and (M7).

All possible physiologically acceptable anions such as chloride, bromide, hydrogen sulfate, methyl sulfate, ethyl sulfate, tetrafluoroborate, phosphate, hydrogen phosphate, dihydrogen phosphate, or p-toluenesulfonate, triflate serve to compensate for the positive polymer charge of copolymers (c2).

If a methosulfate is used to compensate for the positive charge of the polymer of formula (Poly2), these N-methylvinylimidazole/vinylpyrrolidone/vinylcaprolactam copolymers are then referred to according to INCI nomenclature as Polyquaternium-46 and are obtainable, for example, from BASF under the trade name Luviquat® Hold.

Very particularly preferred copolymers (c2) contain 1 to 20 mol %, preferably 5 to 15 mol %, and particularly 10 mol % structural units according to formula (M-11a), and 30 to 50 mol %, preferably 35 to 45 mol %, and particularly 40 mol % structural units according to formula (M6), and 40 to 60 mol %, preferably 45 to 55 mol %, and particularly 60 mol % structural units according to formula (M7).

Particularly preferred agents contain a copolymer (b2) having molar masses within a specific range. Agents according to the present invention wherein copolymer (c2) has a molar mass from 100 to 1000 kDa, preferably 250 to 900 kDa, more preferably 500 to 850 kDa, and particularly 650 to 710 kDa, are preferred here.

In addition to or instead of copolymer or copolymers (c1) and/or (c2), the agents can also contain as a cationic film-forming and/or cationic setting polymer copolymers (c3) having as structural units those of formulas (M11-a) and (M6), as well as further structural units from the group of vinylimidazole units and further structural units from the group of acrylamide and/or methacrylamide units.

Further particularly preferred agents according to the present invention contain as an additional cationic film-forming and/or cationic setting polymer at least one copolymer (c3) having at least one structural unit according to formula (M-11a), at least one structural unit according to formula (M6), at least one structural unit in accordance with formula (M10), and at least one structural unit according to formula (M12)

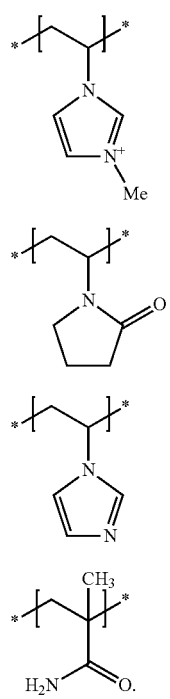

Here, it is particularly preferred if copolymers (c3) contain in addition to polymer units resulting from incorporation of the structural units according to formulae (M11-a), (M6), (M8), and (M12) into the copolymer, up to 5 wt %, preferably up to 1 wt %, of polymer units based on the incorporation of other monomers. Copolymers (c3) are preferably constructed exclusively from structural units of formulas (M11-a), (M6), (M8), and (M12).

All possible physiologically acceptable anions such as chloride, bromide, hydrogen sulfate, methyl sulfate, ethyl sulfate, tetrafluoroborate, phosphate, hydrogen phosphate, dihydrogen phosphate, or p-toluenesulfonate, triflate serve to compensate for the positive polymer charge of component (c3).

If a methosulfate is used to compensate for the positive charge of the polymer of formula (Poly3), these N-methylvinylimidazole/vinylpyrrolidone/vinylimidazole/methacrylamide copolymers are referred to according to INCI nomenclature as Polyquaternium-68 and are obtainable, for example, from BASF under the trade name Luviquat® Supreme.

Very particularly preferred copolymers (c3) contain 1 to 12 mol %, preferably 3 to 9 mol %, and particularly 6 mol % of structural units according to formula (M-11a), and 45 to 65 mol %, preferably 50 to 60 mol %, and particularly 55 mol % of structural units according to formula (M6), and 1 to 20 mol %, preferably 5 to 15 mol %, and particularly 10 mol % of structural units according to formula (M8), and 20 to 40 mol %, preferably 25 to 35 mol %, and particularly 29 mol % of structural units according to formula (M12).

Particularly preferred agents contain a copolymer (c3) having molar masses within a specific range. Agents according to the present invention wherein copolymer (c3) has a molar mass from 100 to 500 kDa, preferably from 150 to 400 kDa, more preferably from 250 to 350 kDa, and particularly from 290 to 310 kDa, are preferred.

Among the additional cationic film-forming and/or setting polymers chosen from cationic polymers having at least one structural element of formula (M11-a), those considered preferred are:
vinylpyrrolidone/1-vinyl-3-methyl-1H-imidazolium chloride copolymers (such as the one having the INCI name Polyquaternium-16 under the commercial designations Luviquat® Style, Luviquat® FC 370, Luviquat® FC 550, Luviquat® FC 905, and Luviquat® HM 552 (BASF SE)),
vinylpyrrolidone/1-vinyl-3-methyl-1H-imidazolium methyl sulfate copolymers (such as the one having the INCI name Polyquaternium-44 under the commercial designations Luviquat® Care (BASF SE)),
vinylpyrrolidone/vinylcaprolactam/1-vinyl-3-methyl-1H-imidazolium terpolymers (such as the one having the INCI name Polyquaternium-46 under the commercial designations Luviquat® Care or Luviquat® Hold (BASF SE)),
vinylpyrrolidone/methacrylamide/vinylimidazole/1-vinyl-3-methyl-1H-imidazolium methyl sulfate copolymers (such as the one having the INCI name Polyquaternium-68 under the commercial designations Luviquat® Supreme (BASF SE)),
as well as mixtures of these polymers.

Further cationic polymers preferably usable in agents according to the present invention are "temporarily cationic" polymers. These polymers usually contain an amino group that is present at certain pH values as a quaternary ammonium group and therefore cationically.

These polymers include chitosans. Chitosan and/or chitosan derivatives are considered very particularly preferably suitable film-forming and/or setting polymers.

Chitosans represent biopolymers, and are hydrocolloids. In chemical terms, they are partially deacetylated chitins of various molecular weights.

The manufacture of chitosans proceeds from chitin, usually crustacean shell residues, which are available in large quantities as cheap raw materials. The chitin is typically first deproteinated by addition of bases, demineralized by adding mineral acids, and lastly deacetylated by adding strong bases. Molecular weights in this context can be distributed over a broad spectrum. It is preferably to use those grades having an average molecular weight from 800,000 to 1,200,000 Dalton, a viscosity per Brookfield (1-wt % in glycolic acid) below 5000 mPa·s, a degree of deacetylation in a range from 80 to 88%, and an ash content of less than 0.3 wt %.

Also appropriate as typical cationic biopolymers in addition to chitosans, are cationically derivatized chitosans (such as quaternization products) or alkoxylated chitosans.

Preferred agents include as (a) chitosan derivative(s) neutralization products of chitosan with at least one acid chosen from lactic acid, formic acid, pyrrolidonecarboxylic acid, nicotinic acid, hydroxyisobutyric acid, hydroxyisovaleric acid, or mixtures of these neutralization products.

Suitable chitosan (derivatives) are readily available commercially, for example, under the trade names Hydagen® CMF (1 wt % active substance in aqueous solution with 0.4 wt % glycolic acid, molecular weight 500,000 to 5,000,000 g/mol, Cognis), Hydagen® HCMF (chitosan (80% deacetylated), molecular weight 50,000 to 1,000,000 g/mol, Cognis), Kytamer® PC (80 wt % active substance as chitosan pyrrolidone carboxylate (INCI name: Chitosan PCA), Amerchol), and Chitolam® NB/101.

The chitosan or derivatives thereof are present in the agents preferably in an amount from 0.01 wt % to 20 wt %, more preferably 0.01 wt % to 10.0 wt %, very preferably 0.1 wt % to 1 wt %, based on weight of the agent.

Likewise considered preferably suitable as temporarily cationic polymers are those having at least one structural unit of formulas (M1-1) to (M1-8)

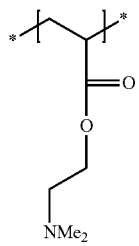

(M1-1)

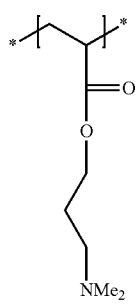

(M1-2)

-continued

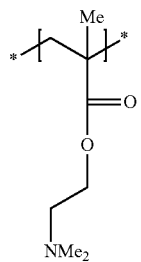

(M1-3)

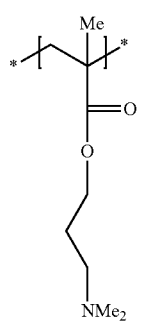

(M1-4)

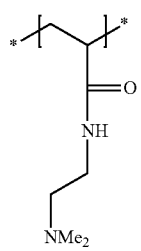

(M1-5)

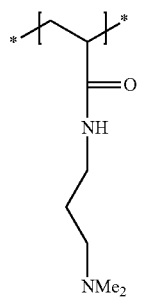

(M1-6)

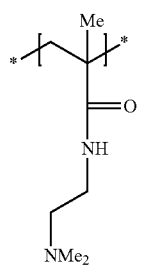

(M1-7)

-continued

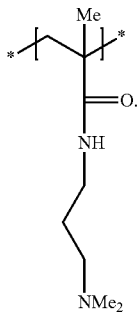
(M1-8)

Those copolymers having at least one structural unit of formulas (M1-1) to (M1-8) and additionally at least one structural unit of formula (M10)

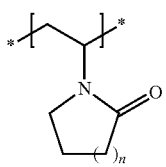
(M10)

wherein n is 1 or 3,
are in turn preferred in this context.

The group of polymers
vinylcaprolactam/vinylpyrrolidone/dimethylaminoethyl methacrylate copolymer (e.g., INCI name: Vinyl Caprolactam/PVP/Di-methylaminoethyl Methacrylate Copolymer, under the trade name Gaffix® VC 713 (ISP)),
vinylpyrrolidone/vinylcaprolactam/dimethylaminopropyl methacrylamide copolymer (e.g., INCI name: VP/Vinyl Caprolactam/DMAPA Acrylates Copolymer, under the trade name Aquaflex SF 40 (ISP)),
vinylcaprolactam/vinylpyrrolidone/dimethylaminoethyl methacrylate copolymer (e.g., as 35 to 39% solids in ethanol in the form of the commercial product Advantage LC E having the INCI name: Vinyl Caprolactam/ VP/Dimethylaminoethyl Methacrylate Copolymer, Alcohol, Laurylpyrrolidone (ISP)),
vinylpyrrolidone/dimethylaminopropylmethacrylamide copolymer (e.g., INCI name: VP/DMAPA Acrylates Copolymer, under the trade name Styleze CC-10 (ISP)),
is considered a preferred list for selection therefrom of at least one or more polymers.

At least one anionic film-forming and/or anionic setting polymer can also be used as film-forming and/or setting polymers.

Anionic polymers are those polymers having carboxylate groups and/or sulfonate groups. Examples of anionic monomers from which such polymers can be made are acrylic acid, methacrylic acid, crotonic acid, maleic acid anhydride, and 2-acrylamido-2-methylpropanesulfonic acid. The acid groups can be present in this context entirely or partially as a sodium, potassium, ammonium, mono- or triethanolammonium salt.

Within this embodiment, it may be preferred to use copolymers of at least one anionic monomer and at least one nonionogenic monomer. Regarding the anionic monomers, reference is made to the substances listed above. Preferred nonionogenic monomers are acrylamide, methacrylamide, acrylic acid esters, methacrylic acid esters, vinylpyrrolidone, vinyl ethers, and vinyl esters.

Preferred anionic copolymers are acrylic acid/acrylamide copolymers, particularly polyacrylamide copolymers with sulfonic acid group-containing monomers. A particularly preferred anionic copolymer is made up of 70 to 55 mol % acrylamide and 30 to 45 mol % 2-acrylamido-2-methylpropanesulfonic acid, the sulfonic acid group being present entirely or partially as a sodium, potassium, ammonium, mono-, or triethanolammonium salt. This copolymer can also be present in crosslinked form, with polyolefinically unsaturated compounds such as tetraallyoxyethane, allylsucrose, allylpentaerythritol, and methylene bisacrylamide preferably being used as crosslinking agents. One such polymer is found in the commercial product Sepigel® 305 of the SEPPIC company. Utilization of this compound, which contains in addition to the polymer component a hydrocarbon mixture (C13 to C14 isoparaffin) and a nonionogenic emulsifier (Laureth-7), has proven particularly advantageous.

Sodium acryloyl dimethyl taurate copolymers marketed, under the trade name Simulgel® 600 as a compound with isohexadecane and polysorbate-80, have also proven particularly effective.

Similarly preferred anionic homopolymers are uncrosslinked and crosslinked polyacrylic acids. Allyl ethers of pentaerythritol, sucrose and propylene can be preferred crosslinking agents. Such compounds are obtainable commercially, for example, under the trademark Carbopol®.

Further anionic polymers usable in preferred fashion are chosen from
copolymers of vinyl acetate and crotonic acid (such as those marketed as a commercial product Aristoflex® A 60, having the INCI name VA/Crotonates Copolymer, by the CIBA company in a 60-wt % dispersion in isopropanol/water),
copolymers of ethyl acrylate and methacrylic acid (such as those marketed under the trade name Luviflex® Soft with an acid number from 84 to 105, under the INCI name Acrylates Copolymer in an approx. 20- to 30-wt % dispersion in water, by the BASF SE company),
polyurethanes having at least one carboxyl group (e.g., a copolymer of isophthalic acid, adipic acid, 1,6-hexanediol, neopentyl glycol, and isophorone diisocyanate, such as the one marketed under the trade name Luviset PUR, having the INCI name Polyurethane-1, by the BASF SE company).

The additional polymers are preferably present in an amount from 0.1 wt % to 15 wt %, particularly 0.5 wt % to 10 wt %, based on weight of the agent.

Agents according to the present invention can also contain at least one amphoteric polymer as a film-forming and/or setting polymer. "Amphoteric polymers" include those polymers having in the molecule both free amino groups and free —COOH or —SO₃H groups and are capable of forming internal salts, and zwitterionic polymers, which contain quaternary ammonium groups and —COO⁻ or —SO₃⁻ groups in the molecule, and those polymers having —COOH or —SO₃H groups and quaternary ammonium groups.

One example of an amphopolymer usable according to the present invention is the acrylic resin obtainable under the name Amphomer®, which represents a copolymer of tert-butylaminoethyl methacrylate, N-(1,1,3,3-tetramethylbutyl) acrylamide, and two or more monomers from the group of acrylic acid, methacrylic acid, and simple alkyl esters thereof.

The amphoteric polymers are present in agents according to the present invention preferably in amounts from 0.01 wt % to 20 wt %, more preferably 0.05 to 10 wt %, based on total agent. Quantities from 0.1 to 5 wt % are very particularly preferred.

Suitable as preferred amphoteric polymers are copolymers formed from
- at least one monomer (Mo1) chosen from acrylic acid, methacrylic acid, acrylic acid alkyl esters, and methacrylic acid alkyl esters, and
- at least one amphoteric monomer (Mo2) chosen from (meth)acrylolyalkylamine oxides of formula (Mo2)

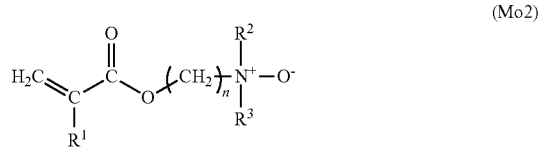

(Mo2)

wherein
$R^1$ is H or CH3,
$R^2$ and $R^3$ are, mutually independently, an optionally branched $C_{1-10}$ alkyl, and
n is a whole number from 1 to 20.

Preferably, n in formula (Mo2) is 2 or 3, and $R^2$ and $R^3$ in formula (Mo2) are, mutually independently, methyl or ethyl.

In a preferred variant of this embodiment, the agent additionally contains at least one copolymer formed from
- at least two monomers (Mo1), the first monomer chosen from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, and methacrylic acid isopropyl ester, and the second monomer chosen from acrylic acid stearyl ester and methacrylic acid stearyl ester, and
- methacryloylethyldimethylamine oxide as monomer (Mo2).

These copolymers are also known, and are obtainable, for example, under the designation Diaformer Z-632 from the Clariant company, with use of Diaformer Z-632 being particularly preferred.

In a further preferred variant of this embodiment, the agent contains at least one copolymer formed from
- at least three monomers (Mo1), the first monomer chosen from acrylic acid, methacrylic acid, acrylic acid methyl ester, methacrylic acid methyl ester, acrylic acid ethyl ester, methacrylic acid ethyl ester, acrylic acid propyl ester, methacrylic acid propyl ester, acrylic acid isopropyl ester, and methacrylic acid isopropyl ester, the second monomer chosen from acrylic acid lauryl ester and methacrylic acid lauryl ester, and the third monomer chosen from acrylic acid stearyl ester and methacrylic acid stearyl ester, and
- methacryloylethyldimethylamine oxide as monomer (Mo2).

Corresponding copolymers are likewise known and are obtainable, for example, from the Clariant company under the designations Diaformer Z-611, Diaformer Z-612, Diaformer Z-613, Diaformer Z-631, Diaformer Z-633, Diaformer Z-651, Diaformer Z-711N, Diaformer Z-712N, and Diaformer Z-731N, with use of Diaformer Z-712N and Diaformer Z-651 being particularly preferred.

Cosmetic agents very particularly preferred according to the present invention conform to at least one of the following embodiments A) to I):

A): A cosmetic agent for temporary deformation of keratinic fibers, particularly human hair, containing, in a cosmetic carrier present in the form of a dispersed system, at least one starch modified with propylene oxide and having an average molecular weight (weight average) from 50 to 2500 kDa, preferably from 100 to 2000 kDa, more preferably from 500 to 1800 kDa, particularly preferably from 700 to 1000 kDa, the starch having a propylene oxide content, based on weight of the starch, from 1 to 20 wt %.

B): A cosmetic agent for temporary deformation of keratinic fibers, particularly human hair, containing, in a cosmetic carrier present in the form of a dispersed system, at least one starch modified with propylene oxide and having an average molecular weight (weight average) from 50 to 2500 kDa, preferably from 100 to 2000 kDa, more preferably from 500 to 1800 kDa, particularly preferably from 700 to 1000 kDa, the starch having a propylene oxide content, based on weight of the starch, from 8.0 to 12.0 wt %.

C): A cosmetic agent for temporary deformation of keratinic fibers, particularly human hair, containing, in a cosmetic carrier present in the form of a dispersed system, at least one starch modified with propylene oxide and having an average molecular weight (weight average) from 50 to 2500 kDa, preferably from 100 to 2000 kDa, more preferably from 500 to 1800 kDa, particularly preferably from 700 to 1000 kDa, the starch having a propylene oxide content, based on weight of the starch, from 9.5 to 10.5 wt % or 4 to 6 wt %.

D): A cosmetic agent for temporary deformation of keratinic fibers, particularly human hair, containing, in a cosmetic carrier present in the form of a dispersed system,
(a) at least one starch modified with propylene oxide and having an average molecular weight (weight average) from 100 to 2000 kDa, preferably from 500 to 1800 kDa, more preferably from 700 to 1000 kDa, the starch having a propylene oxide content, based on weight of the starch, from 1 to 20 wt %, and
(b) at least one additional film-forming and/or setting polymer.

E): A cosmetic agent for temporary deformation of keratinic fibers, particularly human hair, containing, in a cosmetic carrier present in the form of a dispersed system,
(a) at least one starch, modified with propylene oxide, having an average molecular weight (weight average) from 100 to 2000 kDa, preferably from 500 to 1800 kDa, particularly preferably from 700 to 1000 kDa, the starch having a propylene oxide content, based on weight of the starch, from 4 to 12 wt %, and
(b) at least one additional film-forming and/or setting polymer.

F): A cosmetic agent for the temporary deformation of keratinic fibers, particularly human hair, containing, in a cosmetic carrier present in the form of a dispersed system,
(a) at least one starch, modified with propylene oxide, having an average molecular weight (weight average) from 100 to 2000 kDa, preferably from 500 to 1800 kDa, particularly preferably from 700 to 1000 kDa, the starch having a propylene oxide content, based on weight of the starch, from 9.5 to 10.5 wt % or 4 to 6 wt %, and
(b) at least one additional film-forming and/or setting polymer.

G): A cosmetic agent for the temporary deformation of keratinic fibers, particularly human hair, containing, in a cosmetic carrier present in the form of a dispersed system, at least one starch modified with propylene oxide and having an average molecular weight (weight average) from 100 to 2000 kDa, preferably from 500 to 1800 kDa, particularly preferably from 700 to 1000 kDa, as well as a propylene oxide content, based on weight of the starch, from 1 to 20 wt %.

H): A cosmetic agent for the temporary deformation of keratinic fibers, particularly human hair, containing, in a cosmetic carrier present in the form of a dispersed system, at least one starch modified with propylene oxide and having an average molecular weight (weight average) from 100 to 2000 kDa, preferably from 500 to 1800 kDa, particularly preferably from 700 to 1000 kDa, as well as a propylene oxide content, based on weight of the starch, from 4 to 12 wt %.

I): A cosmetic agent for the temporary deformation of keratinic fibers, particularly human hair, containing, in a cosmetic carrier present in the form of a dispersed system, at least one starch modified with propylene oxide and having an average molecular weight (weight average) from 100 to 2000 kDa, preferably from 500 to 1800 kDa, particularly preferably from 700 to 1000 kDa, as well as a propylene oxide content, based on weight of the starch, from 9.5 to 10.5 wt % or 4 to 6 wt %.

The preferred features of the agent according to the present invention, such as utilization quantities, apply mutatis mutandis in the context of the embodiments recited above.

Further addition of at least one compound of formula (I)

$$HO-CH_2-(CHOH)_n-CH_2-OH \quad (I),$$

wherein n is a whole number from 1 to 4, is preferably suitable for improving the effects according to the present invention.

Agents according to the present invention are particularly effective when they contain glycerol and/or sorbitol as compounds of formula (I).

Use of compounds of formula (I) in an amount from 0.2 to 10 wt %, particularly from 0.5 to 7 wt %, has further proven to be advantageous.

It is preferred to additionally use at least one nonionic surfactant. These surfactants can, according to the present invention, have an emulsifying effect.

Nonionic surfactants contain as a hydrophilic group, for example, a polyol group, a polyalkylene glycol ether group, or a combination of a polyol and polyglycol ether group. Such compounds include:

addition products of 2 to 100 mol ethylene oxide and/or 1 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group, addition products of 2 to 20 units of glycerol with linear or branched fatty alcohols having 8 to 30 carbon atoms in the alkyl group, with linear or branched fatty acids having 8 to 30 carbon atoms in the alkyl group such as the grades obtainable under the marketing designations Dermofeel® G 10 LW (Straetmans Chemical Products), addition products, end-capped with a methyl or $C_2$ to $C_6$ alkyl residue, of 2 to 50 mol ethylene oxide and/or 1 to 5 mol propylene oxide with linear and branched fatty alcohols having 8 to 30 carbon atoms, with fatty acids having 8 to 30 carbon atoms, and with alkylphenols having 8 to 15 carbon atoms in the alkyl group, such as the grades obtainable under the marketing designations Dehydrol® LS, Dehydrol® LT (Cognis), $C_{12}$ to $C_{30}$ fatty acid mono- and diesters of addition products of 1 to 30 mol ethylene oxide with glycerol, addition products of 5 to 60 mol ethylene oxide with castor oil and hardened castor oil, polyol fatty acid esters such as the commercial product Hydagen® HSP (Cognis), or Sovermol® grades (Cognis), alkoxylated triglycerides, alkoxylated fatty acid alkyl esters of formula (E4-I)

$$R^1CO-(OCH_2CHR^2)_wOR^3 \quad (E4\text{-}I),$$

wherein $R^1CO$ is a linear or branched, saturated and/or unsaturated acyl residue having 6 to 22 carbon atoms, $R^2$ is hydrogen or methyl, $R^3$ is linear or branched alkyl residues having 1 to 4 carbon atoms, and w is a number from 1 to 20, amine oxides, hydroxy mixed ethers such as those described in German Patent Application No. 19738866, sorbitan fatty acid esters and addition products of ethylene oxide with sorbitan fatty acid esters, for example, polysorbates, sugar fatty acid esters and addition products of ethylene oxide with sugar fatty acid esters, addition products of ethylene oxide with fatty acid alkanolamides and fatty amines, sugar surfactants of the alkyl and alkenyl oligoglycoside types according to formula (E4-II)

$$R^4O-[G]_p \quad (E4\text{-}II),$$

wherein $R^4$ is an alkyl or alkenyl residue having 4 to 22 carbon atoms, G is a sugar residue having 5 or 6 carbon atoms, and p is a number from 1 to 10. They can be obtained according to relevant methods of preparative organic chemistry.

Alkyl oligoglucosides based on hardened $C_{12/14}$ coconut alcohol having a DP from 1 to 3 are preferred.

Particularly preferred nonionic surfactants for use in the agent according to the present invention are those chosen from addition products of 2 to 20 units of glycerol with linear or branched fatty alcohols having 8 to 30 carbon atoms in the alkyl group, addition products of 2 to 20 units of glycerol with linear or branched fatty acids having 8 to 30 carbon atoms in the alkyl group, addition products of 5 to 60 mol ethylene oxide with castor oil and hardened castor oil, sugar surfactants of the alkyl and alkyenyl oligoglycoside types according to the above formula (E4-II), mixtures of the aforesaid surfactants.

Nonionic surfactants are present in the agent preferably in an amount from 0.005 wt % to 10 wt %, particularly 0.01 wt % to 2 wt %, based on total weight of the agent.

Agents according to the invention can also contain at least one plant extract. These extracts are usually produced by extraction of the entire plant. In individual cases, however, it can be preferred to produce the extracts exclusively from blossoms and/or leaves of the plant.

Suitable plant extracts are obtained by extraction using organic solvents (e.g., ethanol, isopropanol, diethyl ether, naphtha, benzene, chloroform) or by steam distillation.

Preferred extracts according to the present invention are from bamboo, linseed, white lotus, green tea, oak bark, nettle, hamamelis, hops, henna, chamomile, burdock root, horsetail, hawthorn, linden blossoms, almond, aloe vera, pine needles, horse chestnut, sandalwood, juniper, coconut, mango, apricot, lemon, wheat, kiwi fruit, melon, orange, grapefruit, salvia, rosemary, birch, mallow, lady's-smock, wild thyme, yarrow, thyme, lemon balm, restharrow, coltsfoot, hibiscus, meristem, ginseng, and ginger root.

The additional plant extract is present in the agent preferably in an amount from 0.05 wt % to 1.0 wt %, particularly 0.1 wt % to 0.5 wt %, based on total weight of the cosmetic agent.

It is particularly preferred if the agent is formulated as a cream, so that the cosmetic agent according to the present invention additionally contain at least one oil phase.

An "oil phase" according to the present invention is a phase, liquid at 20° C., that dissolves at a proportion of less than 1 g in 100 g water at 20° C.

The oil phase preferably has a viscosity of up to 1000 mPas (Brookfield, RVDV II+, 20° C., 20 rpm, spindle 1).

In a preferred embodiment, the oil of the oil phase is chosen from at least one oil of
vegetable oils,
animal oils,
ester oils,
liquid fatty acids and/or their mono-, di-, and trifatty acid esters of saturated and/or unsaturated linear and/or branched $C_6$ to $C_{22}$ fatty acids with glycerol.

Preferred vegetable oils are chosen from at least one of amaranth oil, sunflower oil, olive oil, soy oil, rapeseed oil, castor oil, sesame oil, almond oil, jojoba oil, orange oil, apricot kernel oil, *macadamia* nut oil, wheat germ oil, peach kernel oil, and the liquid components of coconut oil.

Preferred ester oils are chosen from esters of $C_6$ to $C_{30}$ fatty acids with $C_2$ to $C_{30}$ fatty alcohols. Monoesters of fatty acids with alcohols having 2 to 24 carbon atoms are preferred. Examples of fatty acid components used in the esters are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid, and erucic acid, as well as industrial mixtures thereof that occur, for example, upon high-pressure cleavage of natural fats and oils, oxidation of aldehydes from Roelen oxosynthesis, or dimerization of unsaturated fatty acids. Examples of fatty alcohol components in the ester oils are isopropyl alcohol, hexanol, octanol, 2-ethylhexyl alcohol, decanol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol, and brassidyl alcohol, as well as industrial mixtures thereof that occur, for example, upon high-pressure hydrogenation of industrial methyl esters based on fats and oils or aldehydes from Roelen oxosynthesis, and as a monomer fraction upon dimerization of unsaturated fatty alcohols. Particularly preferred ester oils are isopropyl myristate (Rilanit® IPM), isononanoic acid C16-18 alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilane IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V).

Triglyceride esters of capric acid and caprylic acid (INCI name: Caprylic/Capric Triglyceride), obtainable, for example, as a commercial product of the Cognis company under the designation Myritol® 312, are preferred as mono-, di-, and trifatty acid esters of saturated and/or unsaturated linear and/or branched fatty acids with glycerol usable as an oil in the oil phase.

The additional oil phase is present in the agent preferably in an amount from 0.05 wt % to 25 wt %, particularly 0.1 wt % to 20 wt %, based on total weight of the cosmetic agent.

Agents according to the present invention that additionally contain at least one fatty substance are further suitable.

A "fatty substance" according to the present invention is a compound soluble at a proportion of less than 1 g in 100 g water at 20° C.

The fatty substance is preferably chosen from at least one of candelilla wax, shea butter, carnauba wax, beeswax, coconut fat, $C_{12}$ to $C_{20}$ fatty acids (in particular palmitic acid, stearic acid).

The additional fatty substance is present in the agent preferably in an amount from 0.05 wt % to 35 wt %, particularly 1 wt % to 20 wt %, based on total weight of the cosmetic agent.

The following cosmetic agents of embodiments A-1) to I-1), having at least one oil and/or one fatty substance, are preferred according to the present invention:

A-1): A cosmetic agent for temporary deformation of keratinic fibers, particularly human hair, comprising, in a cosmetic carrier present in the form of a dispersed system
water,
at least one nonionic surfactant,
at least one oil and/or one fatty substance, and
at least one starch modified with propylene oxide having an average molecular weight (weight average) from 50 to 2500 kDa, preferably 100 to 2000 kDa, more preferably 500 to 1800 kDa, particularly preferably from 700 to 1000 kDa, the starch having a propylene oxide content, based on weight of the starch, from 1 to 20 wt %.

B-1): A cosmetic agent for temporary deformation of keratinic fibers, particularly human hair, comprising, in a cosmetic carrier present in the form of a dispersed system
water,
at least one nonionic surfactant,
at least one oil and/or one fatty substance, and
at least one starch modified with propylene oxide having an average molecular weight (weight average) from 50 to 2500 kDa, preferably 100 to 2000 kDa, more preferably 500 to 1800 kDa, particularly preferably from 700 to 1000 kDa, the starch having a propylene oxide content, based on weight of the starch, from 8.0 to 12.0 wt %.

C-1): A cosmetic agent for the temporary deformation of keratinic fibers, particularly human hair, comprising, in a cosmetic carrier present in the form of a dispersed system
water,
at least one nonionic surfactant,
at least one oil and/or one fatty substance, and
at least one starch modified with propylene oxide having an average molecular weight (weight average) from 50 to 2500 kDa, preferably 100 to 2000 kDa, more preferably 500 to 1800 kDa, particularly preferably from 700 to 1000 kDa, the starch having a propylene oxide content, based on weight of the starch, from 9.5 to 10.5 wt % or 4 to 6 wt %.

D-1): A cosmetic agent for the temporary deformation of keratinic fibers, particularly human hair, comprising, in a cosmetic carrier present in the form of a dispersed system
water,
at least one nonionic surfactant,
at least one oil and/or one fatty substance,
at least one starch, modified with propylene oxide, having an average molecular weight (weight average) from 100 to 2000 kDa, preferably 500 to 1800 kDa, particularly preferably from 700 to 1000 kDa, the starch having a propylene oxide content, based on weight of the starch, from 1 to 20 wt %, and
at least one additional film-forming and/or setting polymer.

E-1): A cosmetic agent for the temporary deformation of keratinic fibers, particularly human hair, comprising, in a cosmetic carrier present in the form of a dispersed system
- water,
- at least one nonionic surfactant,
- at least one oil and/or one fatty substance,
- at least one starch, modified with propylene oxide, having an average molecular weight (weight average) from 100 to 2000 kDa, preferably 500 to 1800 kDa, particularly preferably from 700 to 1000 kDa, the starch having a propylene oxide content, based on weight of the starch, from 4 to 12 wt %, and
- at least one additional film-forming and/or setting polymer.

F-1): A cosmetic agent for the temporary deformation of keratinic fibers, particularly human hair, comprising, in a cosmetic carrier present in the form of a dispersed system
- water,
- at least one nonionic surfactant,
- at least one oil and/or one fatty substance,
- at least one starch, modified with propylene oxide, having an average molecular weight (weight average) from 100 to 2000 kDa, preferably 500 to 1800 kDa, particularly preferably from 700 to 1000 kDa, the starch having a propylene oxide content, based on weight of the starch, from 9.5 to 10.5 wt % or 4 to 6 we/0, and
- at least one additional film-forming and/or setting polymer.

G-1): A cosmetic agent for the temporary deformation of keratinic fibers, particularly human hair, comprising, in a cosmetic carrier present in the form of a dispersed system
- water,
- at least one nonionic surfactant,
- at least one oil and/or one fatty substance, and
- at least one starch modified with propylene oxide having an average molecular weight (weight average) from 100 to 2000 kDa, preferably 500 to 1800 kDa, particularly preferably from 700 to 1000 kDa, as well as a propylene oxide content, based on weight of the starch, from 1 to 20 wt %.

H-1): A cosmetic agent for the temporary deformation of keratinic fibers, particularly human hair, comprising, in a cosmetic carrier present in the form of a dispersed system
- water,
- at least one nonionic surfactant,
- at least one oil and/or one fatty substance, and
- at least one starch modified with propylene oxide having an average molecular weight (weight average) from 100 to 2000 kDa, preferably from 500 to 1800 kDa, particularly preferably from 700 to 1000 kDa, as well as a propylene oxide content, based on weight of the starch, from 4 to 12 wt %.

I-1): A cosmetic agent for the temporary deformation of keratinic fibers, particularly human hair, comprising, in a cosmetic carrier present in the form of a dispersed system
- water,
- at least one nonionic surfactant,
- at least one oil and/or one fatty substance, and
- at least one starch modified with propylene oxide having an average molecular weight (weight average) from 100 to 2000 kDa, preferably from 500 to 1800 kDa, particularly preferably from 700 to 1000 kDa, as well as a propylene oxide content, based on weight of the starch, from 9.5 to 10.5 wt % or 4 to 6 wt %.

The cosmetic agent according to the present invention can also contain additional adjuvants and additives, preferably using only those raw materials that do not originate in fossil fuels.

Care-providing substances are, in particular, suitable adjuvants and additives.

A cationic surfactant can be used as a care-providing substance. Cationic surfactants of the quaternary ammonium compound, esterquat, and amidoamine types are preferred. Preferred quaternary ammonium compounds are ammonium halides, in particular chlorides and bromides, such as alkyltrimethylammonium chlorides, dialkyldimethylammonium chlorides, and trialkylmethylammonium chlorides (e.g., cetyltrimethylammonium chloride, stearyltrimethylammonium chloride, distearyldimethylammonium chloride, lauryldimethylammonium chloride, lauryldimethylbenzylammonium chloride, and tricetylmethylammonium chloride), as well as the imidazolium compounds known by the INCI names Quaternium-27 and Quaternium-83. Long alkyl chains of the aforementioned surfactants preferably have 10 to 18 carbon atoms. Because addition of surface-active substances can negatively effect the hydrophobic properties of hydrophobized silicon dioxide and thus the stability of the cosmetic agent, the quantity of care-providing surfactant must be carefully coordinated with the overall composition. The addition of surfactant constituents is preferably omitted.

Care-providing polymers are likewise suitable as a care-providing substance.

A first group of care-providing polymers is the cationic polymers. "Cationic polymers" are polymers having in the main chain and/or side chain a group that can be "temporarily" or "permanently" cationic. According to the present invention, those polymers having a cationic group regardless of the pH of the agent are referred to as "permanently cationic". These are polymers having a quaternary nitrogen atom, for example, in the form of an ammonium group. Preferred cationic groups are quaternary ammonium groups.

Cationic polymers further include cationized protein hydrolysates, wherein the underlying protein hydrolysate can derive from animals (e.g., from collagen, milk, or keratin), from plants (e.g., from wheat, corn, rice, potatoes, soy, or almonds), from marine life forms (e.g., from fish collagen or algae), or from biotechnologically obtained protein hydrolysates. Protein hydrolysates serving as the basis for cationic derivatives according to the present invention can be obtained from the corresponding proteins by chemical, particularly alkaline or acid, hydrolysis, by enzymatic hydrolysis, and/or by a combination of the two types of hydrolysis. Hydrolysis of proteins results in a protein hydrolysate having a molecular weight distribution from approximately 100 Dalton up to several thousand Dalton. Those cationic protein hydrolysates whose underlying protein component has a molecular weight from 100 to 25,000 Dalton, preferably 250 to 5,000 Dalton, are preferred. Cationic protein hydrolysates also include quaternized amino acids and mixtures thereof. Quaternization of the protein hydrolysates or of the amino acids is often carried out by quaternary ammonium salts such as N,N-dimethyl-N-(n-alkyl)-N-(2-hydroxy-3-chloro-n-propyl)ammonium halides. The cationic protein hydrolysates can also be further derivatized. Typical examples of cationic protein hydrolysates and derivatives according to the present invention are the products listed under the INCI names in the "International Cosmetic Ingredient Dictionary and Handbook," ($7^{th}$ Edition (1997), The Cosmetic, Toiletry, and Fragrance Association, 1101 $17^{th}$ Street, N.W., Suite 300, Washington, D.C. 20036-4702), and available commercially.

Plant-based cationic protein hydrolysates and derivatives are preferred.

It is further possible to use as a care-providing substance at least one vitamin, provitamin, vitamin precursor, and/or derivative thereof.

Those vitamins, provitamins, and vitamin precursors usually assigned to groups A, B, C, E, F, and H are preferred. Vitamins that belong the B group or to the vitamin B complex are particularly preferred, very particularly preferably vitamin $B_5$ (pantothenic acid, panthenol, and pantolactone).

A number of carboxylic acids are also suitable as a care-providing substance.

Short-chain carboxylic acids, in particular, can be advantageous for purposes of the invention. "Short-chain carboxylic acids" and derivatives thereof refer to carboxylic acids that can be saturated or unsaturated and/or straight-chain or branched or cyclic and/or aromatic and/or heterocylic, and have a molecular weight of less than 750. Saturated or unsaturated straight-chain or branched carboxylic acids having a chain length from 1 to 16 carbon atoms in the chain can be preferred. Those having a chain length from 1 to 12 carbon atoms in the chain are very particularly preferred.

Further suitable care-providing substances are protein hydrolysates and/or derivatives thereof, the use of protein hydrolysates of vegetable origin (e.g., soy, almond, bean, potato, and wheat protein hydrolysates) being preferred. Such products are obtainable, for example, under the trademarks Gluadin® (Cognis), DiaMin® (Diamalt), Lexein® (Inolex), Hydrosoy® (Croda), Hydrolupin® (Croda), Hydrosesame® (Croda), Hydrotritium® (Croda), and Crotein® (Croda).

Although use of protein hydrolysates as such is preferred, it is also optionally possible to use instead of them, if applicable, amino-acid mixtures obtained in different fashion. It is likewise possible to use derivatives of protein hydrolysates, for example, in the form of their fatty acid condensation products. Such products are marketed, for example, under the designations Lamepon® (Cognis), Lexein® (Inolex), Crolastin® (Croda), Crosilk® (Croda), or Crotein® (Croda).

The teaching of the present invention includes all isomeric forms, such as cis-trans isomers, diastereomers, and chiral isomers.

It is also possible according to the present invention to use a mixture of multiple protein hydrolysates.

Also suitable as a care-providing substance are lipids and oily substances, for example, vegetable oils, liquid paraffin oils, isoparaffin oils, synthetic hydrocarbons and ester oils, enzymes, and pearl extracts.

In addition to the care-providing substances, further adjuvants and additives can also be added.

The addition of a UV filter allows both the preparations and the treated fibers to be protected from damaging influences of UV radiation. It can therefore be advantageous to additionally add at least one UV filter to the cosmetic agents. Suitable UV filters are not subject to any general restrictions in terms of their structure and physical properties. Instead, all UV filters usable in the cosmetics sector whose absorption maximum lies in the UVA (315 to 400 nm) UVB (280 to 315 nm), or UVC (<280 nm) regions are suitable. UV filters having an absorption maximum in the UVB region, particularly in the region from approximately 280 to approximately 300 nm, are particularly preferred.

UV filters preferred according to the present invention include substituted benzophenones, p-aminobenzoic acid esters, diphenylacrylic acid esters, cinnamic acid esters, salicylic acid esters, benzimidazoles, and o-aminobenzoic acid esters. Examples that may be recited here are 2-hydroxy-4-methoxybenzophenone-5-sulfonic acid and the sodium salt thereof (Benzophenone-4; Uvinul® MS 40; Uvasorb® S 5).

In a particular embodiment, the cosmetic agent further contains one or more substantive dyes. This allows the keratinic fibers treated with the agent to be not only temporarily structured, but also dyed at the same time. This can be particularly desirable when only a temporary color is desired, for example, with conspicuous "fashion" colors which can be removed again from the keratinic fibers simply by washing.

Cosmetic agents according to the present invention can also contain alkalizing agents, usually alkali hydroxides or alkaline-earth hydroxides, ammonia, or organic amines. Preferred alkalizing agents are monoethanolamine, monoisopropanolamine, 2-amino-2-methylpropanol, 2-amino-2-methyl-1,3-propanediol, 2-amino-2-ethyl-1,3-propanediol, 2-amino-2-methylbutanol, and triethanolamine, as well as alkali metal and alkaline-earth metal hydroxides. Monoethanolamine, triethanolamine, and 2-amino-2-methylpropanol and 2-amino-2-methyl-1,3-propanediol are particularly preferred. Use of ω-amino acids such as ω-aminohexanoic acid as an alkalizing agent is also possible.

Agents according to the present invention are preferably configured as a cream, gel, pump foam or aerosol foam.

If the agents are present in the form of a cream or gel, it is preferred to additionally add at least one polymeric thickening agent. This thickening agent is different from the aforesaid starches modified with propylene oxide. They can be chosen from among polymeric thickening agents known under the following INCI names: Acrylamides Copolymer, Acrylamide/Sodium Acrylate Copolymer, Acrylamide/Sodium Acryloyldimethyltaurate Copolymer, Acrylates/Acetoacetoxyethyl Methacrylate Copolymer, Acrylates/Beheneth-25 Methacrylate Copolymer, Acrylates/C10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, Acrylates/Vinyl Isodecanoate Crosspolymer, Acrylic Acid/Acrylonitrogens Copolymer, Agar, Agarose, *Alcaligenes* Polysaccharides, Algin, Alginic Acid, Ammonium Acrylates/Acrylonitrogens Copolymer, Ammonium Acrylates Copolymer, Ammonium Acryloyldimethyltaurate/Vinyl Formamide Copolymer, Ammonium AcryloyldimethyltaurateNP Copolymer, Ammonium Alginate, Ammonium Polyacryloyldimethyl Taurate, Amylopectin, Ascorbyl Methylsilanol Pectinate, *Astragalus Gummifer* Gum, Attapulgite, *Avena Sativa* (Oat) Kernel Flour, Bentonite, Butoxy Chitosan, *Caesalpinia Spinosa* Gum, Calcium Alginate, Calcium Carboxymethyl Cellulose, Calcium Carrageenan, Calcium Potassium Carbomer, Calcium Starch Octenylsuccinate, C20-40 Alkyl Stearate, Carbomer, Carboxybutyl Chitosan, Carboxymethyl Chitin, Carboxymethyl Chitosan, Carboxymethyl Dextran, Carboxymethyl Hydroxyethylcellulose, Carboxymethyl Hydroxypropyl Guar, Cellulose Acetate Propionate Carboxylate, Cellulose Gum, *Ceratonia Siliqua* Gum, Cetyl Hydroxyethylcellulose, Cholesterol/HDI/Pullulan Copolymer, Cholesteryl Hexyl Dicarbamate Pullulan, *Cyamopsis Tetragonoloba* (Guar) Gum, Diglycol/CHDM/Isophthalates/SIP Copolymer, Dihydrogenated Tallow Benzylmonium Hectorite, Dimethicone Crosspolymer-2, Dimethicone Propyl PG-Betaine, DMAPA Acrylates/Acrylic Acid/Acrylonitrogens Copolymer, Ethylene/Sodium Acrylate Copolymer, Gelatin, Gellan Gum, Glyceryl Alginate, *Glycine Soja* (Soybean) Flour, Guar Hydroxypropyltrimonium Chloride, Hectorite, Hydrated Silica, Hydrogenated Potato Starch, Hydroxybutyl Methylcellulose, Hydroxyethyl Acrylate/Sodium Acryloyldimethyl Taurate Copolymer, Hydroxyethylcellulose, Hydroxyethyl Chitosan, Hydroxyethyl Ethylcellulose, Hydroxypropylcellulose, Hydroxypropyl Chitosan, Hydroxypropyl Ethylenediamine Carbomer, Hydroxypropyl Guar, Hydroxypropyl Methylcellulose, Hydroxypropyl Methylcellulose Stearoxy Ether, Hydroxystearamide MEA, Isobutylene/Sodium Maleate Copolymer, Lithium Magnesium Silicate, Lithium Magnesium Sodium Silicate, *Macrocystis Pyrifera* (Kelp), Magnesium Alginate, Magnesium Aluminum Silicate, Magnesium Silicate, Magnesium Trisilicate, Methoxy PEG-22/Dodecyl Glycol Copolymer, Methylcellulose, Methyl Ethylcellulose, Methyl Hydroxyethylcellulose, Microcrystalline Cellulose, Montmorillonite, Moroccan Lava Clay, Natto Gum, Nonoxynyl Hydroxyethylcellulose, Octadecene/MA Copolymer, Pectin, PEG-800, PEG-Crosspolymer, PEG-150/Decyl Alcohol/SMDI Copolymer, PEG-175 Diisostearate, PEG-190 Distearate, PEG-15 Glyceryl Tristearate, PEG-140 Glyceryl Tristearate, PEG-240/HDI Copolymer Bis-Decyltetradeceth-20 Ether, PEG-100/IPDI Copolymer, PEG-180/Laureth-50/TMMG Copolymer, PEG-10/Lauryl Dimethicone Crosspolymer, PEG-15/Lauryl Dimethicone Crosspolymer, PEG-2M, PEG-5M, PEG-7M, PEG-9M, PEG-14M, PEG-20M, PEG-23M, PEG-25M, PEG-45M, PEG-65M, PEG-90M, PEG-1 15M, PEG-160M, PEG-120 Methyl Glucose Trioleate, PEG-180/Octoxynol-40/TMMG Copolymer, PEG-150 Pentaerythrityl Tetrastearate, PEG-4 Rapeseedamide, PEG-150/Stearyl Alcohol/SMDI Copolymer, Polyacrylate-3, Polyacrylic Acid, Polycyclopentadiene, Polyether-1, Polyethylene/Isopropyl Maleate/MA Copolyol, Polymethacrylic Acid, Polyquaternium-52, Polyvinyl Alcohol, Potassium Alginate, Potassium Aluminum Polyacrylate, Potassium Carbomer, Potassium Carrageenan, Potassium Polyacrylate, Potato Starch Modified, PPG-14 Laureth-60 Hexyl Dicarbamate, PPG-14 Laureth-60 Isophoryl Dicarbamate, PPG-14 Palmeth-60 Hexyl Dicarbamate, Propylene Glycol Alginate, PVP/Decene Copolymer, PVP Montmorillonite, Rhizobian Gum, Ricinoleic Acid/Adipic Acid/AEEA Copolymer, Sclerotium Gum, Sodium Acrylate/Acryloyldimethyl Taurate Copolymer, Sodium Acrylates/Acrolein Copolymer, Sodium Acrylates/Acrylonitrogens Copolymer, Sodium Acrylates Copolymer, Sodium Acrylates/Vinyl Isodecanoate Crosspolymer, Sodium Acrylate/Vinyl Alcohol Copolymer, Sodium Carbomer, Sodium Carboxymethyl Chitin, Sodium Carboxymethyl Dextran, Sodium Carboxymethyl Beta-Glucan, Sodium Carboxymethyl Starch, Sodium Carrageenan, Sodium Cellulose Sulfate, Sodium Cyclodextrin Sulfate, Sodium Hydroxypropyl Starch Phosphate, Sodium Isooctylene/MA Copolymer, Sodium Magnesium Fluorosilicate, Sodium Polyacrylate, Sodium Polyacrylate Starch, Sodium Polyacryloyldimethyl Taurate, Sodium Polymethacrylate, Sodium Polystyrene Sulfonate, Sodium Silicoaluminate, Sodium Starch Octenylsuccinate, Sodium Stearoxy PG-Hydroxyethylcellulose Sulfonate, Sodium Styrene/Acrylates Copolymer, Sodium Tauride Acrylates/Acrylic Acid/Acrylonitrogens Copolymer, *Solanum Tuberosum* (Potato) Starch, Starch/Acrylates/Acrylamide Copolymer, Starch Hydroxypropyltrimonium Chloride, Steareth-60 Cetyl Ether, Steareth-100/PEG-136/HDI Copolymer, *Sterculia Urens* Gum, Synthetic Fluorphlogopite, *Tamarindus Indica* Seed Gum, Tapioca Starch, TEA-Alginate, TEA-Carbomer, *Triticum Vulgare* (Wheat) Starch, Tromethamine Acrylates/Acrylonitrogens Copolymer, Tromethamine Magnesium Aluminum Silicate, Welan Gum, Yeast Beta-Glucan, Yeast Polysaccharides, *Zea Mays* (Corn) Starch.

Particularly preferably, the polymeric thickener is chosen from polymeric, anionic, amphiphilic thickeners, particularly preferably from those having the INCI names Acrylates/Beheneth-25 Methacrylate Copolymer, Acrylates/C10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-20 Acrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, Acrylates/Vinyl Isodecanoate Crosspolymer, Acrylates/Steareth-20 Methacrylate Crosspolymer.

Polymeric thickening agents are present in the agent in cream form or gel form preferably in an amount from 0.5 to 20 wt %, particularly from 0.5 to 10 wt %.

Preferably, the gel is a transparent gel.

Very particularly preferred cosmetic agents according to the present invention comply with at least one of the following embodiments A-2) to I-2):

A-2): A cosmetic agent for temporary deformation of keratinic fibers, particularly human hair, comprising, in a cosmetic carrier present in the form of a gel,
    at least one polymeric thickening agent,
    at least one starch modified with propylene oxide having an average molecular weight (weight average) from 50 to 2500 kDa, preferably 100 to 2000 kDa, more preferably 500 to 1800 kDa, particularly preferably from 700 to 1000 kDa, the starch having a propylene oxide content, based on weight of the starch, from 1 to 20 wt %.

B-2): A cosmetic agent for temporary deformation of keratinic fibers, particularly human hair, comprising, in a cosmetic carrier present in the form of a gel,
    at least one polymeric thickening agent,
    at least one starch modified with propylene oxide having an average molecular weight (weight average) from 50 to 2500 kDa, preferably 100 to 2000 kDa, more preferably 500 to 1800 kDa, particularly preferably from 700 to 1000 kDa, the starch having a propylene oxide content, based on weight of the starch, from 8.0 to 12.0 wt %.

C-2): A cosmetic agent for temporary deformation of keratinic fibers, particularly human hair, comprising, in a cosmetic carrier present in the form of a gel,
    at least one polymeric thickening agent,
    at least one starch modified with propylene oxide having an average molecular weight (weight average) from 50 to 2500 kDa, preferably 100 to 2000 kDa, more preferably 500 to 1800 kDa, particularly preferably from 700 to 1000 kDa, the starch having a propylene oxide content, based on weight of the starch, from 9.5 to 10.5 wt % or 4 to 6 wt %.

D-2): A cosmetic agent for temporary deformation of keratinic fibers, particularly human hair, comprising, in a cosmetic carrier present in the form of a gel,
    at least one polymeric thickening agent,
    at least one starch modified with propylene oxide having an average molecular weight (weight average) from 100 to 2000 kDa, preferably 500 to 1800 kDa, particularly preferably from 700 to 1000 kDa, the starch having a propylene oxide content, based on weight of the starch, from 1 to 20 wt %, and
    at least one additional film-forming and/or setting polymer.

E-2): A cosmetic agent for temporary deformation of keratinic fibers, particularly human hair, comprising, in a cosmetic carrier present in the form of a gel,
    at least one polymeric thickening agent,
    at least one starch modified with propylene oxide having an average molecular weight (weight average) from 100 to 2000 kDa, preferably 500 to 1800 kDa, particularly preferably from 700 to 1000 kDa, the starch having a propylene oxide content, based on weight of the starch, from 4 to 12 wt %, and at least one additional film-forming and/or setting polymer.

F-2): A cosmetic agent for temporary deformation of keratinic fibers, particularly human hair, comprising, in a cosmetic carrier present in the form of a dispersed system, at least one starch, modified with propylene oxide, having an average molecular weight (weight average) from 100 to 2000 kDa, preferably 500 to 1800 kDa, particularly preferably from 700 to 1000 kDa, the starch having a propylene oxide content, based on weight of the starch, from 9.5 to 10.5 wt % or 4 to 6 wt %, and at least one additional film-forming and/or setting polymer.

G-2): A cosmetic agent for temporary deformation of keratinic fibers, particularly human hair, comprising, in a cosmetic carrier present in the form of a gel, at least one polymeric thickening agent, at least one starch modified with propylene oxide having an average molecular weight (weight average) from 100 to 2000 kDa, preferably 500 to 1800 kDa, particularly preferably from 700 to 1000 kDa, as well as a propylene oxide content, based on weight of the starch, from 1 to 20 wt %.

H-2): A cosmetic agent for temporary deformation of keratinic fibers, particularly human hair, comprising, in a cosmetic carrier present in the form of a gel, at least one polymeric thickening agent, at least one starch modified with propylene oxide having an average molecular weight (weight average) from 100 to 2000 kDa, preferably 500 to 1800 kDa, particularly preferably from 700 to 1000 kDa, as well as a propylene oxide content, based on weight of the starch, from 4 to 12 wt %.

I-2): A cosmetic agent for temporary deformation of keratinic fibers, particularly human hair, comprising, in a cosmetic carrier present in the form of a gel, at least one polymeric thickening agent, at least one starch modified with propylene oxide having an average molecular weight (weight average) from 100 to 2000 kDa, preferably 500 to 1800 kDa, particularly preferably from 700 to 1000 kDa, as well as a propylene oxide content, based on weight of the starch, from 9.5 to 10.5 wt % or 4 to 6 wt %.

The preferred features of the agent according to the present invention such as, in particular, utilization quantities, apply mutatis mutandis in the embodiments recited above.

In addition, anionic, amphiphilic, polymeric thickening agents, in particular, are also particularly preferred in embodiments A-2) to I-2) as polymeric thickening agents.

At least one copolymer according to claim 14 is considered a particularly preferred additional film-forming and/or setting polymer in the embodiments A-2) to I-2).

If the agents are in the form of foam, they are discharged from a delivery apparatus suitable for foaming that is either a pressurized-gas container additionally filled with propellant ("aerosol container"), or a non-aerosol container. Here, the dispersed system of the cosmetic carrier is present as foam.

The pressurized gas container by which a product is distributed through a valve as a result of the internal gas pressure of the container is referred to as an "aerosol container." A "non-aerosol container" is, conversely to the "aerosol" definition, a vessel under standard pressure by which a product is distributed by mechanical action using a pump system.

Agents according to the present invention are particularly preferably present as aerosol hair foam. The agent therefore preferably additionally contains at least one propellant.

Agents according to the present invention that are present in the form of an aerosol product can be manufactured in usual fashion. Typically, all constituents of the agent according to the present invention except the propellant are introduced into a suitable pressure-tight container. The container is then sealed with a valve. Lastly, the desired quantity of propellant is introduced using conventional techniques.

Propellants suitable according to the present invention for generating aerosol foam are chosen, for example, from $N_2O$, dimethyl ether, $CO_2$, air, alkanes having 3 to 5 carbon atoms such as propane, n-butane, isobutane, n-pentane, and isopentane, and mixtures thereof. Dimethyl ether, propane, n-butane, isobutane, and mixtures thereof are preferred.

In order to foam gel-type agents in a two-chamber aerosol container, isopentane is preferably suitable as a propellant that is incorporated into agents according to the present invention and is packaged in the first chamber of the two-chamber aerosol container. Packaged in the second chamber of the two-chamber aerosol container is at least one further propellant different from isopentane that builds up in the two-chamber aerosol container a higher pressure than the isopentane. Propellants of the second chamber are preferably chosen from $N_2O$, dimethyl ether, $CO_2$, air, alkanes having 3 or 4 carbon atoms (such as propane, n-butane, isobutane), and mixtures thereof.

For a given spray apparatus, the sizes of the foam bubbles and the respective size distribution can be adjusted by way of the quantitative ratio between the propellant and the other constituents of the preparations.

When conventional aerosol containers are used, aerosol foam products contain propellant preferably in amounts from 1 to 35 wt %, based on total product. Quantities from 2 to 30 wt %, particularly 3 to 15 wt %, are particularly preferred.

Use of additional preferred ingredients recited above, and of the utilization quantities or utilization quantity ratios identified as preferred (see above), is also preferred in this/these embodiment(s).

A second subject of the invention is the use of a cosmetic agent of the first subject of the invention for temporary deformation and/or shape fixing of keratinic fibers, particularly human hair.

A third subject of the invention is a method for temporary deformation of keratinic fibers, particularly human hair, wherein a cosmetic agent of the first subject of the invention is applied onto the keratinic fibers.

It is preferred if the keratinic fibers, after application of the cosmetic agents of the first subject of the invention, are not rinsed and are left on the fibers.

The Examples that follow are intended to explain the subject matter of the present invention without limiting them in any way.

EXAMPLES

The following commercial products were used:

| | |
|---|---|
| Abil Quat 3272 | Polysiloxane terminated with 3-(3-((3-cocoamidopropyl)dimethylammonio)-2-hydroxypropyl)propyl groups (50 wt % active substance in |

| Advantage ® LC-A | 1,2-propylene glycol; INCI name: Quaternium-80) (Goldschmidt) Vinylcaprolactam/vinylpyrrolidone/dimethylaminoethyl methacrylate copolymer (approx. 35 to 39% solids in ethanol; INCI name: Vinyl Caprolactam/VP/Dimethylaminoethyl Methacrylate Copolymer, Alcohol) (ISP) |
|---|---|
| Aculyn ® 28 | Copolymer of (meth)acrylic acid, (meth)acrylic acid ester and beheneth-25-methacrylic acid ester (19 to 21 wt % solids in water; INCI name: Acrylates/Beheneth-25 Methacrylate Copolymer) (Rohm and Haas) |
| Amaze | Nonionic, modified corn starch (INCI name: Corn Starch Modified) (National Starch) |
| Antaron ® WP-660 | Copolymer of vinylpyrrolidone and 1-triacontene (INCI name: Tricontanyl PVP) (ISP) |
| Celquat ® L 200 | Quaternized cellulose derivative (INCI name: Polyquaternium-4) (National Starch) |
| Crodafos ® CES | INCI name: Cetearyl Alcohol, Dicetyl Phosphate, Ceteth-10 Phosphate (Croda) |
| Dekafald | 1,3-Dihydroxymethyl-5,5-dimethylhydantoin (approx. 54 to 56 wt % active substance in water; INCI name: DMDM Hydantoin) (Jan Dekker) |
| Dow Corning ® 556 | Polyphenylmethylsiloxane (INCI name: Phenyl Trimethicone) (Dow Corning) |
| Edenor L2SM | Mixture of palmitic acid and stearic acid (INCI name: Palmitic Acid, Stearic Acid) (Cognis) |
| Euxyl ® K 320 | Mixture of phenoxyethanol, methylparaben, ethylparaben, propylene glycol (Schülke & Mayr) |
| Dow Corning ® 939 | Approx. 32 to 36% solids; INCI name: Amodimethicone, Trideceth-12, Cetrimonium Chloride (Dow Corning) |
| Dow Corning ® 959 | 52 to 37% solids; INCI name: Amodimethicone, Trideceth-12, Cetrimonium Chloride (Dow Corning) |
| Gafquat ® 755N PW | Dimethylaminoethylmethacrylate/vinylpyrrolidone copolymer, quaternized with diethyl sulfate (approx. 19% solids in water; INCI name: Polyquaternium-11) (ISP) |
| Genamin ® CTAC | Trimethylhexadecylammonium chloride (approx. 28 to 30% active substance in water; INCI name: Cetrimonium Chloride) (Clariant) |
| Luviskol ® VA 64 W | Copolymer of vinylpyrrolidone and vinyl acetate (60:40) (48 to 52% active substance in water, INCI name: VP VA Copolymer) (BASF) |
| Luviskol ® K85 | Polyvinylpyrrolidone (approx. 20% solids in water; INCI name: PVP) (BASF) |
| Luviskol ® K90 | Polyvinylpyrrolidone (approx. 20% solids in water; INCI name: PVP) (BASF) |
| Luviskol VA 73 W | Vinylpyrrolidone/vinyl acetate copolymer (70:30) (approx. 48 to 52% solids in water; INCI name: VP/VA Copolymer) (BASF) |
| Neolone ® PE | 2-Methyl-2H-isothiazolin-3-one (approx. 1.55% in 2-phenoxyethanol; INCI name: Phenoxyethanol, Methylisothiazolinone) (Rohm & Haas) |
| Pemulen ® TR-1 | Branched acrylic acid polymer (INCI name: Acrylates/C10-30 Alkyl Acrylate Crosspolymer) (Lubrizol) |
| Silsoft Q | 31 wt % in water (INCI name: Aqua (Water), Silicone Quaternium-18, Trideceth-6, Trideceth-12) (Momentive) |
| Styleze ® CC 10 | Copolymer of N-vinylpyrrolidone and N,N-dimethylaminopropylmethacrylamide (approx. 9 to 11% active substance, INCI name: VP/DMAPA Acrylates Copolymer) (ISP) |
| Uvinul ® P 25 | 4-Aminobenzoic acid ethyl ester + 25 mol ethylene oxide (INCI name: PEG-25 PABA) (BASF SE) |
| Tylose H 100000 YP2 | Hydroxyethyl cellulose (90 wt % active substance; INCI name: Hydroxyethylcellulose) (SE Tylose) |
| Xiameter PMX 200 Sil Fluid 50 CS | Polydimethylsiloxane (INCI name: Dimethicone, viscosity: 50 cSt) (Xiameter) |

1.0 Styling Creams—

| Raw material | C1 | I1 | I2 | I3 |
|---|---|---|---|---|
| Disodium EDTA | 0.05 | 0.05 | — | — |
| 1,2-Propanediol | 1.50 | 1.50 | — | — |
| Starch modified with propylene oxide[1] | — | 30.00 | 3.00 | 20.00 |
| Methylparaben | 0.13 | 0.13 | 0.10 | — |
| Propylparaben | 0.03 | 0.03 | — | — |
| Tylose H 100000 YP2 | 0.30 | 0.30 | — | — |
| Amaze | 0.50 | 0.50 | — | — |
| Pemulen TR-1 | — | — | 0.30 | 0.20 |
| Aculyn 88 | — | — | 6.00 | — |
| Soft ceresin FL 400 | 2.00 | 2.00 | — | 6.00 |
| Crodafos CES | 1.50 | 1.50 | — | 1.00 |
| Estol 3752 | 0.30 | 0.30 | — | — |

-continued

| Raw material | C1 | I1 | I2 | I3 |
|---|---|---|---|---|
| Cetyl alcohol | 0.75 | 0.75 | — | 2.00 |
| Diisopropyl adipate | — | — | 0.20 | — |
| Benzoic acid ($C_{12}$ to $C_{15}$) alkyl ester | — | — | — | 5.00 |
| Paraffinum liquidum | — | — | — | 1.00 |
| Beeswax | — | — | — | 5.00 |
| Xiameter PMX 200 Sil Fluid 50 CS | — | — | 0.30 | 0.50 |
| Silsoft Q | — | — | 0.50 | — |
| Dow Corning 556 | — | — | 1.00 | — |
| Dow Corning 959 | — | — | 0.50 | — |
| Abil Quat 3272 | — | — | 1.00 | — |
| Cetyltrimethylammonium chloride | — | — | 0.30 | — |
| Antaron WP-660 | 1.50 | 1.50 | — | — |
| Stearyl alcohol | 0.75 | 0.75 | — | — |
| Steareth-21 | 0.75 | 0.75 | — | 1.10 |
| Edenor L2SM | — | — | — | 7.50 |
| Steareth-2 | — | — | — | 1.50 |
| Oleth-20 | — | — | — | 1.00 |
| PPG-5-Ceteth-20 | — | — | — | 1.00 |
| Advantage LC-A | 10.00 | — | — | — |
| Luviskol VA 73 W | 10.00 | — | — | — |
| Luviskol K 85 | — | 10.00 | — | — |
| Luviskol K 90 | 20.00 | — | — | — |
| Styleze CC-10 | 10.00 | 10.00 | — | — |
| Dekafald | 0.30 | — | — | — |
| 2-Phenoxyethanol | — | 0.50 | — | 0.40 |
| Glycerol | — | — | 1.50 | — |
| D-Panthenol | — | — | 0.20 | — |
| Neolone PE | — | — | 0.30 | 0.50 |
| 2-Amino-2-methylpropanol | — | — | 0.50 | — |
| Lactic acid | — | 2.00 | — | — |
| Perfume | 0.70 | 0.70 | 0.30 | 0.90 |
| Water | to 100 | to 100 | to 100 | to 100 |

[1] Tapioca starch modified with 10 wt % propylene oxide, average molecular weight 800 kDa, viscosity of a 43-wt % solution in water = 64,000 mPa·s 1.2 Styling Gels—

| Raw material | I4 | I5 | I6 | I7 |
|---|---|---|---|---|
| Disodium EDTA | — | — | 0.05 | — |
| 1,2-Propanediol | 6.00 | — | — | — |
| Starch modified with propylene oxide[1] | 9.50 | 12.00 | 12.00 | 2.00 |
| Methylparaben | 0.10 | — | — | — |
| Propylparaben | — | — | — | — |
| Aculyn 28 | 3.00 | — | — | — |
| Aculyn 88 | — | — | — | 2.30 |
| Synthalen W 2000 | — | — | — | 1.80 |
| Polygel W 30 | — | 3.00 | — | — |
| Structure 2001 | — | — | 5.00 | — |
| PEG-40 Hydrogenated Castor Oil | 0.40 | — | — | 0.20 |
| PPG-5-Ceteth-20 | — | — | 0.50 | — |
| Euxyl K320 | — | — | — | 1.00 |
| Luviskol K 90 | — | — | 12.00 | — |
| Luviskol K 85 | — | 5.00 | — | — |
| Polyethylene glycol 1500 | 2.00 | — | — | — |
| Dekafald | — | — | — | — |
| 2-Phenoxyethanol | — | — | — | — |
| Glycerol | 10.00 | 2.75 | 2.00 | — |
| D-Panthenol | 0.15 | — | 0.20 | 0.20 |
| Neolone PE | 0.30 | 0.60 | 0.60 | — |
| Triethanolamine | — | — | — | 0.80 |
| Lactic acid | — | 0.10 | 0.30 | — |
| Uvinul P25 | — | — | — | 0.05 |
| Perfume | 0.15 | 0.20 | 0.20 | 0.20 |
| Water | to 100 | to 100 | to 100 | to 100 |

[1] Tapioca starch modified with 10 wt % propylene oxide, average molecular weight 800 kDa, viscosity of a 43-wt % solution in water = 64,000 mPa·s 1.3 Styling Foams (Aerosol)—

| Raw material | C2 | I7 |
|---|---|---|
| Celquat L 200 | 0.30 | 0.30 |
| Luviskol VA 64 W | 2.00 | — |
| Starch modified with propylene oxide[1] | — | 2.00 |
| Gafquat 755N PW | 7.40 | 7.40 |
| D-Panthenol | 0.20 | 0.20 |
| Glycerol | 0.15 | 0.15 |
| Dow Corning 939 | 0.20 | 0.20 |
| Genamin CTAC | 1.00 | 1.00 |
| PEG 40 Hydrogenated Castor Oil | 0.30 | 0.30 |
| Perfume | 0.15 | 0.20 |
| Water | to 100 | to 100 |

[1] Tapioca starch modified with 10 wt % propylene oxide, average molecular weight 800 kDa, viscosity of a 43-wt % solution in water = 64,000 mPa·s Formulations C2 and I7 were each placed into an aerosol container that meets the following technical parameters: aluminum reservoir container having a valve (product 522983 PV10697 of the Precision company (Deutsche Prazisions-Ventil GmbH).

The aerosol container was filled with a propellant gas mixture of propane/butane (47 wt % propane, 50 wt % butane, 3 wt % isobutane), yielding a weight ratio of formulation to propellant gas of 92 to 8.

2.0 Demonstration of Effectiveness—

Of the compositions listed above, Agents I1, I1, C1, and C2 were compared with one another by way of example, The following results were obtained:

a) Hair foams a1) Hold, elasticity, and flexibility (omega loop method)

TABLE 2

| Hold, elasticity, flexibility - | | | |
|---|---|---|---|
| Composition | F max (N) | Elasticity | Flexibility |
| I7 | 2.2 | 60 | 75 |
| C2 | 1.9 | 50 | 80 |

The higher the F max values, the better the hairstyle hold. The values in Table 2 confirm that propylene oxide-modified starch derivatives according to the present invention yield a hairstyle hold that is comparable to—and in fact, when the propylene oxide-modified starch derivative has a low molecular weight, is even better than—the common film former PVP/VA.

The higher the values for elasticity or flexibility, the better the elasticity or flexibility of the hairstyle. Hair strands treated with agents according to the present invention exhibited a more flexible and more elastic hold than the strands that had been treated with PVP/VA copolymer.

a2) High humidity curl retention (HHCR)

TABLE 3

| High humidity curl retention (HHCR) - | |
|---|---|
| Composition | HHCR |
| I7 | 50 |
| C2 | 20 |

The hair strands treated with the agent according to the present invention exhibited a hairstyle hold that was more resistant to humidity.

b) Hair gels b1) Hold, elasticity, flexibility

TABLE 4

| Composition | Hold, elasticity, flexibility - | | |
|---|---|---|---|
| | F max (N) | Elasticity | Flexibility |
| I7 | 4.1 | 66 | 88 |
| C2 | 3.3 | 55 | 85 |

The higher the F max values, the better the hairstyle hold. The values in Table 4 confirm that propylene oxide-modified starch derivatives according to the present invention yield a hairstyle hold that is comparable to—and in fact, when the propylene oxide-modified starch derivative has a low molecular weight, is even better than—the common film former PVP/VA.

The higher the values for elasticity resp. flexibility, the better the elasticity resp. flexibility of the hairstyle. The hair strands treated with the agents according to the present invention exhibited a more flexible and more elastic hold than the strands that had been treated with PVP/VA copolymer.

3.0 Performing the Omega Loop Measurement—

Deformation hold (also called "hairstyle hold") as well as flexibility and elasticity were determined for purposes of the present invention using the omega loop method.

For this, a dry hair strand (European Natural hair of the Kerling company, bonded dense tress, bonded at one end, total length 160 mm, free length 150 mm, width 10 mm, weight 1.0±0.1 g) is immersed as far as the lower edge of the adhesive bond for 30 seconds into the polymer solution to be investigated. The excess solution is then wiped off between the thumb and forefinger so that 0.5±0.02 g of solution remains on the hair. The hair strand, saturated with the solution to be investigated, is wound around a Teflon cylinder 36 mm in diameter and the projecting ends are secured with a clip. The prepared strands are then dried and conditioned in an environmental chamber overnight at 25° C. and 50% relative humidity, or at 25° C. and 75% relative humidity.

The conditioned strand is carefully removed from the Teflon cylinder. The resulting omega loop—a ring-shaped structure of hair stabilized in shape by the polymer film that has formed—is clamped into the grippers mounted on the load cell and lowered to just above the baseplate of an AMETEK LF Plus universal testing instrument of AMETEK Precision Instruments Europe GmbH, Lloyd product group. The entire measurement is performed in an environmental chamber under constant climatic conditions, at 25° C. and 50% relative humidity or at 25° C. and 75% relative humidity.

In order to create standardized initial conditions, measurement begins with application of a preload of 0.07 N at a rate of 30 mm min$^{-1}$. The omega loop is then compressed 8 mm at a rate of 60 mm min$^{-1}$, the required force being measured. Once the characteristic force F1 at the maximum deformation of 8 mm has been recorded, the strand is unloaded at 60 mm min$^{-1}$ until it has risen 10 mm from the baseplate. The next cycle begins from there, by once again applying the 0.07 N preload and then compressing the strand 8 mm; the applicable rates are the same as described above. Measurement of one omega loop includes a total of 10 cycles.

Four characteristic parameters for describing the mechanical properties of film-forming polymers can be determined using this measurement method. The hold, flexibility, plasticity, and elasticity can be calculated from the measured forces using the following formulas:

$$\text{Hold} = F_1 [N]$$

($F_1$ corresponds to maximum measurement force)

$$\text{Flexibility} = \frac{F_{10}}{F_1}$$

(indicates the ratio of maximum forces between the tenth and the first cycle)

$$\text{Elasticity} = \frac{\frac{F_{10}(2\,mm) - F_{10}(1,5\,mm)}{0,5}}{\frac{F_1(2\,mm) - F_1(1,5\,mm)}{0,5}} = \frac{E_{10}}{E_1}$$

(to calculate the elasticity, the forces for a 1.5 mm and 2 mm deformation are acquired respectively from the first and the tenth cycle, and are correlated).

4.0 Performing the High Humidity Curl Retention Measurement—

Standardized hair strands of the Kerling company (item no. 827560), hair type "European Natural," color 6/0, with a length (Lmax) of 220 mm and a weight of 0.6 g, were used. For preparation, the strands were washed with 12.5-wt % sodium laureth sulfate solution. The hair strands were dried overnight in a drying oven at 318° K.

0.18 g of the compositions was respectively applied onto each hair strand and massaged in. The strands were then wound onto a curler (Fripac-medis, diam. 7 mm, item no. D-1203) and dried overnight at room temperature.

The curlers were then carefully removed, and the strands were suspended. The length of each of the curls was measured (L0), and the strands were put into a climate chamber. They were stored there at 294° K and a relative humidity of 85% for a period of 24 hours, and the lengths of the curls were then measured again ($L_t$).

Five test strands were correspondingly treated and measured for each composition.

High humidity curl retention (HHCR) was calculated using the formula below, and the arithmetic mean of HHCR values for the five test strands was obtained for each composition:

$$HHCR = \frac{L_{max} - L_t}{L_{max} - L_0}$$

We claim:

1. Cosmetic agent for temporary deformation of keratinic fibers comprising, in a cosmetic carrier present in the form of a dispersed system:
   at least one starch modified with propylene oxide and having an average molecular weight (weight average) from 50 to 2500 kDa; and
   wherein the modified starch has a propylene oxide content of 1 to 20 wt % based on the weight of the modified starch.

2. Cosmetic agent according to claim 1, wherein the modified starch comprises an average molecular weight (weight average) from 100 to 2000 kDa.

3. Cosmetic agent according to claim 2, wherein the modified starch comprises an average molecular weight (weight average) from 500 to 1800 kDa.

4. Cosmetic agent according to claim 2, wherein the modified starch comprises an average molecular weight (weight average) from 700 to 1000 kDa.

5. Cosmetic agent according to claim 1, wherein the modified starch has, in a 43-wt % aqueous solution, a viscosity from 150 to 1,500,000 mPa·s, based on Brookfield viscosimeter, spindle 7 at 20° C. and 20 rpm.

6. Cosmetic agent according to claim 1, wherein the modified starch has an amylose content of less than 25 wt %, based on the weight of the starch.

7. Cosmetic agent according to claim 1 comprising at least one uncrosslinked starch modified with propylene oxide.

8. Cosmetic agent according to claim 1, wherein the agent is a cream or gel.

9. Cosmetic agent according to claim 8 further comprising at least one polymeric thickening agent.

10. Cosmetic agent according to claim 9, wherein the polymeric thickener is a polymeric, anionic, amphiphilic thickener.

11. Cosmetic agent according to claim 10, wherein the polymeric thickener is chosen from those having the INCI names Acrylates/Beheneth-25 Methacrylate Copolymer, Acrylates/C10-30 Alkyl Acrylate Crosspolymer, Acrylates/Ceteth-20 Itaconate Copolymer, Acrylates/Ceteth-20 Methacrylate Copolymer, Acrylates/Laureth-25 Methacrylate Copolymer, Acrylates/Palmeth-20 Acrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Stearyl Methacrylate Copolymer, Acrylates/Vinyl Isodecanoate Crosspolymer, and Acrylates/Steareth-20 Methacrylate Crosspolymer.

12. Cosmetic agent according to claim 1, wherein the agent is a foam and is discharged from a delivery apparatus suitable for foaming.

13. Cosmetic agent according to claim 12, wherein the delivery apparatus is a pressurized-gas container additionally filled with a propellant ("aerosol container") or a non-aerosol container.

14. Cosmetic agent according to claim 1, wherein the modified starch is present in an amount from 0.1 wt % to 80 wt %, based on weight of the agent.

15. Cosmetic agent according to claim 12, wherein the modified starch is present in an amount from 0.1 wt % to 80 wt %, based on weight of the agent.

16. Cosmetic agent according to claim 1 further comprising at least one film-forming and/or setting polymer.

17. Cosmetic agent according to claim 16, wherein the at least one additional film-forming and/or setting polymer is at least one copolymer comprising at least one monomer (Mo1) chosen from acrylic acid, methacrylic acid, acrylic acid alkyl esters, and methacrylic acid alkyl esters, and at least one amphoteric monomer (Mo2) chosen from (meth)acryloylalkylamine oxides of formula (Mo2)

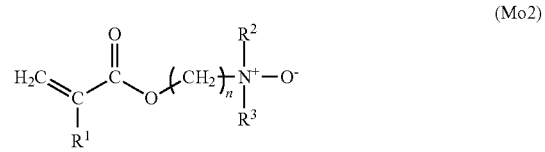

(Mo2)

wherein $R^1$ is H or $CH_3$, $R_2$ and $R_3$ are, mutually independently, optionally branched $C_{1-10}$ alkyl, and n is a whole number from 1 to 20.

* * * * *